United States Patent
Katnani et al.

(10) Patent No.: US 11,515,014 B2
(45) Date of Patent: Nov. 29, 2022

(54) METHODS AND SYSTEMS FOR INITIATING AND CONDUCTING A CUSTOMIZED COMPUTER-ENABLED BRAIN RESEARCH STUDY

(71) Applicant: HI LLC, Los Angeles, CA (US)

(72) Inventors: Husam Katnani, Braintree, MA (US); Antonio H. Lara, Valencia, CA (US); Alejandro Ojeda, Culver City, CA (US); Julien Dubois, Santa Monica, CA (US); Viktoria Rojkova, Los Angeles, CA (US); Bryan Johnson, Culver City, CA (US); Gabriel Lerner, Los Angeles, CA (US)

(73) Assignee: HI LLC, Los Angeles, CA (US)

( * ) Notice: Subject to any disclaimer, the term of this patent is extended or adjusted under 35 U.S.C. 154(b) by 23 days.

(21) Appl. No.: 17/176,321

(22) Filed: Feb. 16, 2021

(65) Prior Publication Data

US 2021/0265025 A1   Aug. 26, 2021

Related U.S. Application Data

(60) Provisional application No. 63/126,933, filed on Dec. 17, 2020, provisional application No. 62/979,852, filed on Feb. 21, 2020.

(51) Int. Cl.
*G16H 10/20* (2018.01)
*G06Q 30/00* (2012.01)
*G16H 80/00* (2018.01)

(52) U.S. Cl.
CPC .......... *G16H 10/20* (2018.01); *G06Q 30/018* (2013.01); *G16H 80/00* (2018.01)

(58) Field of Classification Search
CPC ....... G16H 10/20; G16H 80/00; G06Q 30/018
See application file for complete search history.

(56) References Cited

U.S. PATENT DOCUMENTS

| | | |
|---|---|---|
| 4,018,534 A | 4/1977 | Thorn et al. |
| 4,207,892 A | 6/1980 | Binder |

(Continued)

FOREIGN PATENT DOCUMENTS

| | | |
|---|---|---|
| CN | 200950235 | 9/2007 |
| CN | 107865635 | 4/2018 |

(Continued)

OTHER PUBLICATIONS

"emojipedia.org", https://emojipedia.org (accessed May 27, 2021).

(Continued)

*Primary Examiner* — Eliza A Lam
(74) *Attorney, Agent, or Firm* — ALG Intellectual Property, LLC

(57) ABSTRACT

An illustrative research support computing system maintains subject data representative of attributes for research subjects included in a potential subject pool for potential research studies. The system receives, from a client device, an input dataset representative of: 1) a set of parameters defining a research study to be conducted with respect to a research subject group, and 2) a set of criteria for research subjects that are to be included in the research subject group. The system designates a research subject included in the potential subject pool for inclusion in the research subject group based on the set of criteria, and receives research data detected for the research subject in accordance with the set of parameters. The system also provides an output dataset generated based on the research data detected for the research subject in accordance with the set of parameters. Corresponding methods and systems are also disclosed.

30 Claims, 14 Drawing Sheets

(56) References Cited

U.S. PATENT DOCUMENTS

| | | |
|---|---|---|
| 4,281,645 A | 8/1981 | Jobsis |
| 4,321,930 A | 3/1982 | Jobsis |
| 4,515,165 A | 5/1985 | Carroll |
| 4,655,225 A | 4/1987 | Dahne et al. |
| 4,928,248 A | 5/1990 | Takahashi et al. |
| 4,963,727 A | 10/1990 | Cova |
| 4,995,044 A | 2/1991 | Blazo |
| 5,088,493 A | 2/1992 | Giannini |
| 5,090,415 A | 2/1992 | Yamashita |
| 5,309,458 A | 5/1994 | Carl |
| 5,386,827 A | 2/1995 | Chance et al. |
| 5,528,365 A | 6/1996 | Gonatas et al. |
| 5,625,458 A | 4/1997 | Alfano et al. |
| 5,761,230 A | 6/1998 | Oono et al. |
| 5,853,370 A | 12/1998 | Chance et al. |
| 5,895,984 A | 4/1999 | Renz |
| 5,929,982 A | 7/1999 | Anderson |
| 5,983,120 A | 11/1999 | Groner et al. |
| 5,987,045 A | 11/1999 | Albares et al. |
| 6,163,715 A | 12/2000 | Larsen et al. |
| 6,240,309 B1 | 5/2001 | Yamashita et al. |
| 6,384,663 B2 | 5/2002 | Cova et al. |
| 6,541,752 B2 | 4/2003 | Zappa et al. |
| 6,640,133 B2 | 10/2003 | Yamashita |
| 6,683,294 B1 | 1/2004 | Herbert et al. |
| 6,748,254 B2 | 6/2004 | O'Neil |
| 6,992,772 B2 | 1/2006 | Block |
| 7,095,491 B2 | 8/2006 | Forstner et al. |
| 7,356,365 B2 | 4/2008 | Schurman |
| 7,507,596 B2 | 3/2009 | Yaung et al. |
| 7,547,872 B2 | 6/2009 | Niclass et al. |
| 7,613,504 B2 | 11/2009 | Rowe |
| 7,667,400 B1 | 2/2010 | Goushcha |
| 7,705,284 B2 | 4/2010 | Inoue et al. |
| 7,714,292 B2 | 5/2010 | Agarwal et al. |
| 7,774,047 B2 | 8/2010 | Yamashita et al. |
| 7,899,506 B2 | 3/2011 | Xu et al. |
| 8,026,471 B2 | 9/2011 | Itzler |
| 8,078,250 B2 | 12/2011 | Chen et al. |
| 8,082,015 B2 | 12/2011 | Yodh et al. |
| 8,115,170 B2 | 2/2012 | Stellari et al. |
| 8,168,934 B2 | 5/2012 | Niclass et al. |
| 8,352,012 B2 | 1/2013 | Besio |
| 8,633,431 B2 | 1/2014 | Kim |
| 8,637,875 B2 | 1/2014 | Finkelstein et al. |
| 8,754,378 B2 | 6/2014 | Prescher et al. |
| 8,817,257 B2 | 8/2014 | Herve |
| 8,937,509 B2 | 1/2015 | Xu et al. |
| 8,986,207 B2 | 3/2015 | Li |
| 9,012,860 B2 | 4/2015 | Nyman et al. |
| 9,041,136 B2 | 5/2015 | Chia |
| 9,058,081 B2 | 6/2015 | Baxter |
| 9,076,707 B2 | 7/2015 | Harmon |
| 9,101,279 B2 | 8/2015 | Ritchey et al. |
| 9,131,861 B2 | 9/2015 | Ince et al. |
| 9,157,858 B2 | 10/2015 | Claps |
| 9,160,949 B2 | 10/2015 | Zhang et al. |
| 9,176,241 B2 | 11/2015 | Frach |
| 9,178,100 B2 | 11/2015 | Webster et al. |
| 9,190,552 B2 | 11/2015 | Brunel et al. |
| 9,201,138 B2 | 12/2015 | Eisele et al. |
| 9,209,320 B1 | 12/2015 | Webster |
| 9,257,523 B2 | 2/2016 | Schneider et al. |
| 9,257,589 B2 | 2/2016 | Niclass et al. |
| 9,299,732 B2 | 3/2016 | Webster et al. |
| 9,299,873 B2 | 3/2016 | Mazzillo et al. |
| 9,312,401 B2 | 4/2016 | Webster |
| 9,316,735 B2 | 4/2016 | Baxter |
| 9,331,116 B2 | 5/2016 | Webster |
| 9,368,487 B1 | 6/2016 | Su et al. |
| 9,401,448 B2 | 7/2016 | Bienfang et al. |
| 9,407,796 B2 | 8/2016 | Dinten et al. |
| 9,419,635 B2 | 8/2016 | Kumar et al. |
| 9,431,439 B2 | 8/2016 | Soga et al. |
| 9,442,201 B2 | 9/2016 | Schmand et al. |
| 9,449,377 B2 | 9/2016 | Sarkar et al. |
| 9,450,007 B1 | 9/2016 | Motta et al. |
| 9,466,631 B2 | 10/2016 | Fallica et al. |
| 9,476,979 B2 | 10/2016 | Drader et al. |
| 9,478,579 B2 | 10/2016 | Dai et al. |
| 9,529,079 B1 | 12/2016 | Droz |
| 9,535,157 B2 | 1/2017 | Caley et al. |
| 9,574,936 B2 | 2/2017 | Heinonen |
| 9,625,580 B2 | 4/2017 | Kotelnikov et al. |
| 9,627,569 B2 | 4/2017 | Harmon |
| 9,639,063 B2 | 5/2017 | Dutton et al. |
| 9,640,704 B2 | 5/2017 | Frey et al. |
| 9,658,158 B2 | 5/2017 | Renna et al. |
| 9,659,980 B2 | 5/2017 | McGarvey et al. |
| 9,671,284 B1 | 6/2017 | Dandin |
| 9,681,844 B2 | 6/2017 | Xu et al. |
| 9,685,576 B2 | 6/2017 | Webster |
| 9,702,758 B2 | 7/2017 | Nouri |
| 9,728,659 B2 | 8/2017 | Hirigoyen et al. |
| 9,741,879 B2 | 8/2017 | Frey et al. |
| 9,753,351 B2 | 9/2017 | Eldada |
| 9,767,246 B2 | 9/2017 | Dolinsky et al. |
| 9,768,211 B2 | 9/2017 | Harmon |
| 9,773,930 B2 | 9/2017 | Motta et al. |
| 9,804,092 B2 | 10/2017 | Zeng et al. |
| 9,812,438 B2 | 11/2017 | Schneider et al. |
| 9,831,283 B2 | 11/2017 | Shepard et al. |
| 9,851,302 B2 | 12/2017 | Mattioli Della Rocca et al. |
| 9,867,250 B1 | 1/2018 | Powers et al. |
| 9,869,753 B2 | 1/2018 | Eldada |
| 9,881,963 B1 | 1/2018 | Chen et al. |
| 9,882,003 B1 | 1/2018 | Aharoni |
| 9,886,095 B2 | 2/2018 | Pothier |
| 9,899,544 B1 | 2/2018 | Mazzillo et al. |
| 9,899,557 B2 | 2/2018 | Muscara' et al. |
| 9,939,316 B2 | 4/2018 | Scott et al. |
| 9,939,536 B2 | 4/2018 | O'Neill et al. |
| 9,946,344 B2 | 4/2018 | Ayaz et al. |
| D817,553 S | 5/2018 | Aaskov et al. |
| 9,983,670 B2 | 5/2018 | Coleman |
| 10,016,137 B1 | 7/2018 | Yang et al. |
| D825,112 S | 8/2018 | Saez |
| 10,056,415 B2 | 8/2018 | Na et al. |
| 10,103,513 B1 | 10/2018 | Zhang et al. |
| 10,141,458 B2 | 11/2018 | Zhang et al. |
| 10,157,954 B2 | 12/2018 | Na et al. |
| 10,158,038 B1 | 12/2018 | Do Valle et al. |
| 10,219,700 B1 | 3/2019 | Yang et al. |
| 10,256,264 B2 | 4/2019 | Na et al. |
| 10,340,408 B1 | 7/2019 | Katnani |
| 10,424,683 B1 | 9/2019 | Do Valle |
| 10,483,125 B2 | 11/2019 | Inoue |
| 10,515,993 B2 | 12/2019 | Field et al. |
| 10,533,893 B2 | 1/2020 | Leonardo |
| 10,558,171 B2 | 2/2020 | Kondo |
| 10,627,460 B2 | 4/2020 | Alford et al. |
| 10,697,829 B2 | 6/2020 | Delic |
| 10,772,561 B2 | 9/2020 | Donaldson |
| 10,809,796 B2 | 10/2020 | Armstrong-Muntner |
| 10,825,847 B2 | 11/2020 | Furukawa |
| 10,912,504 B2 | 2/2021 | Nakaji |
| 10,976,386 B2 | 4/2021 | Alford |
| 10,983,177 B2 | 4/2021 | Jiménez-Martínez |
| 10,996,293 B2 | 5/2021 | Mohseni |
| 11,006,876 B2 | 5/2021 | Johnson |
| 11,006,878 B2 | 5/2021 | Johnson |
| 2004/0057478 A1 | 3/2004 | Saito |
| 2004/0078216 A1* | 4/2004 | Toto ............... G16H 10/60 705/2 |
| 2004/0160996 A1 | 8/2004 | Giorgi et al. |
| 2005/0061986 A1 | 3/2005 | Kardynal et al. |
| 2006/0197452 A1 | 9/2006 | Zhang |
| 2007/0038116 A1 | 2/2007 | Yamanaka |
| 2007/0083097 A1 | 4/2007 | Fujiwara |
| 2008/0021341 A1* | 1/2008 | Harris ............... A61B 5/4094 600/544 |
| 2009/0012402 A1 | 1/2009 | Mintz |
| 2009/0163775 A1 | 6/2009 | Barrett |

(56) References Cited

U.S. PATENT DOCUMENTS

| | | | |
|---|---|---|---|
| 2009/0313048 A1* | 12/2009 | Kahn | G16H 20/10 705/3 |
| 2010/0151014 A1* | 6/2010 | Liang | A61K 31/485 424/457 |
| 2010/0210952 A1 | 8/2010 | Taira et al. | |
| 2011/0208675 A1 | 8/2011 | Shoureshi et al. | |
| 2012/0029304 A1 | 2/2012 | Medina et al. | |
| 2012/0101838 A1* | 4/2012 | Lingard | G06Q 10/10 705/2 |
| 2013/0030267 A1 | 1/2013 | Lisogurski | |
| 2013/0032713 A1 | 2/2013 | Barbi et al. | |
| 2013/0144644 A1* | 6/2013 | Simpson | G16H 10/20 705/2 |
| 2013/0221221 A1 | 8/2013 | Bouzid et al. | |
| 2013/0342835 A1 | 12/2013 | Blacksberg | |
| 2014/0027607 A1 | 1/2014 | Mordarski et al. | |
| 2014/0066783 A1 | 3/2014 | Kiani | |
| 2014/0185643 A1 | 7/2014 | McComb et al. | |
| 2014/0191115 A1 | 7/2014 | Webster et al. | |
| 2014/0211194 A1 | 7/2014 | Pacala et al. | |
| 2014/0275891 A1 | 9/2014 | Muehlemann et al. | |
| 2014/0289001 A1 | 9/2014 | Shelton | |
| 2014/0291481 A1 | 10/2014 | Zhang et al. | |
| 2015/0041625 A1 | 2/2015 | Dutton | |
| 2015/0041627 A1 | 2/2015 | Webster | |
| 2015/0054111 A1 | 2/2015 | Niclass et al. | |
| 2015/0057511 A1 | 2/2015 | Basu | |
| 2015/0077279 A1 | 3/2015 | Song | |
| 2015/0094552 A1 | 4/2015 | Golda | |
| 2015/0150505 A1 | 6/2015 | Kaskoun et al. | |
| 2015/0182136 A1 | 7/2015 | Durduran et al. | |
| 2015/0192677 A1 | 7/2015 | Yu et al. | |
| 2015/0200222 A1 | 7/2015 | Webster | |
| 2015/0293224 A1 | 10/2015 | Eldada et al. | |
| 2015/0327777 A1 | 11/2015 | Kostic et al. | |
| 2015/0333095 A1 | 11/2015 | Fallica et al. | |
| 2015/0364635 A1 | 12/2015 | Bodlovic et al. | |
| 2016/0049765 A1 | 2/2016 | Eldada | |
| 2016/0099371 A1 | 4/2016 | Webster | |
| 2016/0119983 A1 | 4/2016 | Moore | |
| 2016/0150963 A1 | 6/2016 | Roukes et al. | |
| 2016/0161600 A1 | 6/2016 | Eldada et al. | |
| 2016/0181302 A1 | 6/2016 | McGarvey et al. | |
| 2016/0218236 A1 | 7/2016 | Dhulla et al. | |
| 2016/0247301 A1 | 8/2016 | Fang | |
| 2016/0278715 A1 | 9/2016 | Yu et al. | |
| 2016/0287107 A1 | 10/2016 | Szabados | |
| 2016/0341656 A1 | 11/2016 | Liu et al. | |
| 2016/0345880 A1 | 12/2016 | Nakaji et al. | |
| 2016/0356718 A1 | 12/2016 | Yoon et al. | |
| 2016/0357260 A1 | 12/2016 | Raynor et al. | |
| 2017/0030769 A1 | 2/2017 | Clemens et al. | |
| 2017/0047372 A1 | 2/2017 | McGarvey et al. | |
| 2017/0052065 A1 | 2/2017 | Sharma et al. | |
| 2017/0118423 A1 | 4/2017 | Zhou et al. | |
| 2017/0124713 A1 | 5/2017 | Jurgenson et al. | |
| 2017/0131143 A1 | 5/2017 | Andreou et al. | |
| 2017/0139041 A1 | 5/2017 | Drader et al. | |
| 2017/0141100 A1 | 5/2017 | Tseng et al. | |
| 2017/0176579 A1 | 6/2017 | Niclass et al. | |
| 2017/0176596 A1 | 6/2017 | Shpunt et al. | |
| 2017/0179173 A1 | 6/2017 | Mandai et al. | |
| 2017/0186798 A1 | 6/2017 | Yang et al. | |
| 2017/0202518 A1 | 7/2017 | Furman et al. | |
| 2017/0265822 A1 | 9/2017 | Du | |
| 2017/0276545 A1 | 9/2017 | Henriksson | |
| 2017/0281086 A1 | 10/2017 | Donaldson | |
| 2017/0299700 A1 | 10/2017 | Pacala et al. | |
| 2017/0303789 A1 | 10/2017 | Tichauer et al. | |
| 2017/0314989 A1 | 11/2017 | Mazzillo et al. | |
| 2017/0363467 A1 | 12/2017 | Clemens et al. | |
| 2018/0003821 A1 | 1/2018 | Imai | |
| 2018/0014741 A1 | 1/2018 | Chou | |
| 2018/0019268 A1 | 1/2018 | Zhang et al. | |
| 2018/0020960 A1 | 1/2018 | Sarussi | |
| 2018/0026147 A1 | 1/2018 | Zhang et al. | |
| 2018/0027196 A1 | 1/2018 | Yang et al. | |
| 2018/0033895 A1 | 2/2018 | Mazzillo et al. | |
| 2018/0039053 A1 | 2/2018 | Kremer et al. | |
| 2018/0045816 A1 | 2/2018 | Jarosinski et al. | |
| 2018/0062345 A1 | 3/2018 | Bills et al. | |
| 2018/0069043 A1 | 3/2018 | Pan et al. | |
| 2018/0070830 A1 | 3/2018 | Sutin et al. | |
| 2018/0070831 A1 | 3/2018 | Sutin et al. | |
| 2018/0081061 A1 | 3/2018 | Mandai et al. | |
| 2018/0089531 A1 | 3/2018 | Geva et al. | |
| 2018/0089848 A1 | 3/2018 | Yang et al. | |
| 2018/0090526 A1 | 3/2018 | Mandai et al. | |
| 2018/0090536 A1 | 3/2018 | Mandai et al. | |
| 2018/0102442 A1 | 4/2018 | Wang et al. | |
| 2018/0103528 A1 | 4/2018 | Moore | |
| 2018/0103861 A1 | 4/2018 | Sutin et al. | |
| 2018/0156660 A1 | 6/2018 | Turgeon | |
| 2018/0167606 A1 | 6/2018 | Cazaux et al. | |
| 2018/0175230 A1 | 6/2018 | Droz et al. | |
| 2018/0185667 A1 | 7/2018 | Huang | |
| 2018/0217261 A1 | 8/2018 | Wang | |
| 2018/0296094 A1 | 10/2018 | Nakamura | |
| 2018/0366342 A1 | 12/2018 | Inoue et al. | |
| 2019/0006399 A1 | 1/2019 | Otake et al. | |
| 2019/0026849 A1 | 1/2019 | Demeyer | |
| 2019/0076375 A1* | 3/2019 | De Wilde | A61K 31/7068 |
| 2019/0088697 A1 | 3/2019 | Furukawa et al. | |
| 2019/0091483 A1 | 3/2019 | Deckert | |
| 2019/0113385 A1 | 4/2019 | Fukuchi | |
| 2019/0167211 A1* | 6/2019 | Everman | A61B 5/0205 |
| 2019/0175068 A1 | 6/2019 | Everdell | |
| 2019/0200888 A1* | 7/2019 | Poltorak | A61B 5/165 |
| 2019/0261869 A1 | 8/2019 | Franceschini | |
| 2019/0298158 A1 | 10/2019 | Dhaliwal | |
| 2019/0343395 A1 | 11/2019 | Cussac | |
| 2019/0355773 A1 | 11/2019 | Field et al. | |
| 2019/0355861 A1 | 11/2019 | Katnani | |
| 2019/0363210 A1 | 11/2019 | Do Valle | |
| 2019/0378869 A1 | 12/2019 | Field et al. | |
| 2019/0388018 A1 | 12/2019 | Horstmeyer | |
| 2019/0391213 A1 | 12/2019 | Alford | |
| 2020/0056263 A1 | 2/2020 | Bhattacharyya | |
| 2020/0057115 A1 | 2/2020 | Jiménez-Martínez | |
| 2020/0057116 A1 | 2/2020 | Zorzos et al. | |
| 2020/0088811 A1 | 3/2020 | Mohseni | |
| 2020/0109481 A1 | 4/2020 | Sobek | |
| 2020/0123416 A1 | 4/2020 | Bhattacharyya | |
| 2020/0182692 A1 | 6/2020 | Lilic | |
| 2020/0191883 A1 | 6/2020 | Bhattacharyya | |
| 2020/0196932 A1 | 6/2020 | Johnson | |
| 2020/0241094 A1 | 7/2020 | Alford | |
| 2020/0256929 A1 | 8/2020 | Ledbetter et al. | |
| 2020/0309873 A1 | 10/2020 | Ledbetter et al. | |
| 2020/0315510 A1 | 10/2020 | Johnson | |
| 2020/0334559 A1 | 10/2020 | Anderson | |
| 2020/0337624 A1 | 10/2020 | Johnson | |
| 2020/0341081 A1 | 10/2020 | Mohseni et al. | |
| 2020/0348368 A1 | 11/2020 | Garber et al. | |
| 2020/0381128 A1 | 12/2020 | Pratt | |
| 2020/0390358 A1 | 12/2020 | Johnson | |
| 2020/0393902 A1 | 12/2020 | Mann et al. | |
| 2020/0400763 A1 | 12/2020 | Pratt | |
| 2021/0015385 A1 | 1/2021 | Katnani | |
| 2021/0011094 A1 | 2/2021 | Bednarke | |
| 2021/0041512 A1 | 2/2021 | Pratt | |
| 2021/0063510 A1 | 3/2021 | Ledbetter | |
| 2021/0013974 A1 | 5/2021 | Seidman | |
| 2021/0139742 A1 | 5/2021 | Seidman | |

FOREIGN PATENT DOCUMENTS

| | | |
|---|---|---|
| EP | 0656536 | 4/2004 |
| EP | 2294973 | 3/2011 |
| EP | 3419168 | 12/2018 |
| EP | 3487072 | 5/2019 |
| WO | 8804034 | 6/1988 |
| WO | 1999053577 | 10/1999 |
| WO | 2008144831 | 12/2008 |

(56) References Cited

FOREIGN PATENT DOCUMENTS

| WO | 2012135068 | 10/2012 |
|---|---|---|
| WO | 2013034770 | 3/2013 |
| WO | 2013066959 | 5/2013 |
| WO | 2015052523 | 4/2015 |
| WO | 2015109005 | 7/2015 |
| WO | 2016166002 | 10/2016 |
| WO | 2017004663 | 1/2017 |
| WO | 2017130682 | 8/2017 |
| WO | 2017150146 | 9/2017 |
| WO | 2017203936 | 11/2017 |
| WO | 2018007829 | 1/2018 |
| WO | 2018033751 | 2/2018 |
| WO | 2018122560 | 7/2018 |

OTHER PUBLICATIONS

"International Search Report and Written Opinion received in International Application No. PCT/2021/018188".

"International Search Report and Written Opinion received in International Application No. PCT/US2021/018155".

"International Search Report and Written Opinion received in International Application No. PCT/US2021/018187".

"International Search Report and Written Opinion received in International Application No. PCT/US2021/018190".

"scienceofpeople.com/emojis", https://www.scienceofpeople.com/emojis/ (accessed May 27, 2021).

Hebert, et al.,"Spatiotemporal image correlation spectroscopy (STICS) theory, verification, and application to protein velocity mapping in living CHO cells", Biophysical journal 88, No. 5 (2005): 3601-3614.

Kheng, et al.,"Image Processing", https://www.comp.nus.edu.sg/~cs4243/lecture/imageproc.pdf, Mar. 9, 2014.

Sneha, et al.,"Understanding Correlation", https://www.allaboutcircuits.com/technical-articles/understanding-correlation/, Jan. 4, 2017.

Xu, et al.,"A 655 µW Silicon Photomultiplier-Based NIRS/EEG/EIT Monitoring ASIC for Wearable Functional Brain Imaging", IEEE Transactions on Biomedical Circuits and Systems, IEEE, US, vol. 12, No. 6, Dec. 1, 2018.

Zucconi, et al.,"The Autocorrelation Function", https://www.alanzucconi.com/2016/06/06/autocorrelation-function/, Jun. 6, 2016.

Alayed, et al., Characterization of a Time-Resolved Diffuse Optical Spectroscopy Prototype Using Low-Cost, Compact Single Photon Avalanche Detectors for Tissue Optics Applications, Sensors 2018, 18, 3680; doi: 10.3390/s18113680.

Bellis, Stephen et al., "Photon counting imaging: the DigitalAPD," Society of Photo-Optical Instrumentation Engineers (SPIE) Conference Series, Feb. 2006, vol. 6068, pp. 111-120.

Blutman, et al., "A 0.1 pJ Freeze Vernier Time-to-Digital Converter in 65nm CMOS," 2014 International Symposium on Circuits and Systems (ISCAS), Melbourne, Australia.

Cambie, Dario et al., "Every photon counts: understanding and optimizing photon paths in luminescent solar concentrator-based photomicroreactors (LSC-PMs)," React. Chem. Eng., 2017, 2, 561-566.

Contini, et al., "Photon migration through a turbid slab described by a model based on diffusion approximation. I. Theory," Appl. Opt. 36(19), 4587 (1997).

Dalla Mora, et al., "Fast-Gated Single-Photon Avalanche Diode for Wide Dynamic Range Near Infrared Spectroscopy," IEEE Journal of Selected Topics in Quantum Electronics, vol. 16, No. 4, Jul./Aug. 2010, 2010, 1023-1030.

Dalla Mora, et al., "Memory effect in silicon time-gated single-photon avalanche diodes," http://dx.doi.org/10.1063/1.4915332, Journal of Applied Physics 117, 114501, 2015, 2015, 1-7.

De Heyn, et al., "A fast start-up 3GHz-10GHz digitally controlled oscillator for UWB impulse radio in 90nm CMOS," 2007 European Solid-State Circuits Conference—(ESSCIRC), Munich, Germany, pp. 484-487.

Di Sieno, et al., "Probe-hosted large area silicon photomultiplier and high-throughput timing electronics for enhanced performance time-domain functional near-infrared spectroscopy," Biomed. Opt. Express 11(11), 6389 (2020).

Dutton, et al., "A Time-Correlated Single-Photon-Counting Sensor with 14GS/s Histogramming Time-to-Digital Converter," 2015 IEEE International Solid-State Circuits Conference ISSCC 2015 / Session 11 / Sensors and Imagers for Life Sciences / 11.5.

Fishburn, et al., "Temporal Derivative Distribution Repair (TDDR): A motion correction method for fNIRS," NeuroImage, Jan. 1, 2019; 184: 171-179. doi:10.1016/j.neuroimage.2018.09.025.

Fisher, et al., "A Reconfigurable Single-Photon-Counting Integrating Receiver for Optical Communications," IEEE Journal of Solid-State Circuits, vol. 48, No. 7, Jul. 2013, https://www.researchgate.net/publication/260626902.

Gallivanoni, et al., "Progress in Quenching Circuits for Single Photon Avalanche Diodes," IEEE Transactions on Nuclear Science, vol. 57, No. 6, Dec. 2010.

Gnecchi, et al., "A 1×16 SIPM Array for Automotive 3D Imaging LiDAR Systems."

Harmon, Eric S. et al., "Compound Semiconductor SPAD Arrays," Lightspin Technologies, http://www.lightspintech.com/publications.html.

Henderson, et al., "A 192×128 Time Correlated SPAD Image Sensor in 40-nm CMOS Technology," IEEE Journal of Solid-State Circuits, IEEE Journal of Solid-State Circuits, 2019.

Henderson, et al., "A 256×256 40nm/90nm CMOS 3D-Stacked 120dB Dynamic-Range Reconfigurable Time-Resolved SPAD Imager," 2019 IEEE International Solid-State Circuits Conference—(ISSCC), San Francisco, CA, USA, 2019, pp. 106-103. doi: 10.1109/ISSCC.2019.8662355.

Huppert, et al., "HomER: a review of time-series analysis methods for near-infrared spectroscopy of the brain," Appl. Opt. 48(10), D280 (2009).

Kienle, et al., "Improved solutions of the steady-state and the time-resolved diffusion equations for reflectance from a semi-infinite turbid medium," J. Opt. Soc. Am. A 14(1), 246 (1997).

Konugolu, et al., "Broadband (600-1350 nm) Time-Resolved Diffuse Optical Spectrometer for Clinical Use," IEEE Journal of Selected Topics in Quantum Electronics, vol. 22, No. 3, May/Jun. 2016.

Lacerenza, et al., "Wearable and wireless time-domain near-infrared spectroscopy system for brain and muscle hemodynamic monitoring," Biomed. Opt. Express 11(10), 5934 (2020).

Lange, et al., "Clinical Brain Monitoring with Time Domain NIRS: A Review and Future Perspectives," Applied Sciences 9(8), 1612 (2019).

Lange, et al., "MAESTROS: A Multiwavelength Time-Domain NIRS System to Monitor Changes in Oxygenation and Oxidation State of Cytochrome-C-Oxidase," IEEE J. Select. Topics Quantum Electron. 25(1), 1-12 (2019).

Lee, et al., "High-Performance Back-Illuminated Three-Dimensional Stacked Single-Photon Avalanche Diode Implemented in 45-nm CMOS Technology," IEEE Journal of Selected Topics in Quantum Electronics 6, 1-9 (2018).

Mandai, et al., "A 4 X 4 X 416 digital SiPM array with 192 TDCs for multiple high-resolution timestamp acquisition," 2013 JINST 8 P05024.

Martelli, et al., "Optimal estimation reconstruction of the optical properties of a two-layered tissue phantom from time-resolved single-distance measurements," Journal of Biomedical Optics 20(11), 115001 (Nov. 2015).

Maruyama, et al., "A 1024×8, 700-ps Time-Gated SPAD Line Sensor for Planetary Surface Exploration With Laser Raman Spectroscopy and LIBS," IEEE Journal of Solid-State Circuits, vol. 49, No. 1, Jan. 2014, 2014, 179-189.

Mita, et al., "High-Speed and Compact Quenching Circuit for Single-Photon Avalanche Diodes," IEEE Transactions on Instrumentation and Measurement, vol. 57, No. 3, Mar. 2008. pp. 543-547.

Mora, et al., "Fast silicon photomultiplier improves signal harvesting and reduces complexity in time-domain diffuse optics," Opt. Express 23(11), 13937 (2015).

(56) References Cited

OTHER PUBLICATIONS

Mora, Alberto D. et al., "Fast-Gated Single-Photon Avalanche Diode for Wide Dynamic Range Near Infrared Spectroscopy," IEEE Journal of Selected Topics in Quantum Electronics, vol. 16, No. 4, pp. 1023-1030, Jul./Aug. 2010.
Parmesan, et al., "A 256×256 SPAD array with in-pixel Time to Amplitude Conversion for Fluorescence Lifetime Imaging Microscopy," 2015.
Pifferi, et al., "Performance assessment of photon migration instruments: the MEDPHOT protocol," Applied Optics, 44(11), 2104-2114.
Prahl, et al., "Optical Absorption of Hemoglobin," http://omic.ogi.edu/spectra/hemoglobin/index.html.
Puszka, et al., "Time-resolved diffuse optical tomography using fast-gated single-photon avalanche diodes," Biomedical optics express, 2013, vol. 4, No. 8, pp. 1351-1365 (Year: 2013).
Re, et al., "Multi-channel medical device for time domain functional near infrared spectroscopy based on wavelength space multiplexing," Biomed. Opt. Express 4(10), 2231 (2013).
Renna, et al., "Eight-Wavelength, Dual Detection Channel Instrument for Near-Infrared Time-Resolved Diffuse Optical Spectroscopy," IEEE J. Select. Topics Quantum Electron. 25(1), 1-11 (2019).
Richardson, et al., "A 32×32 50ps resolution 10 bit time to digital converter array in 130nm CMOS for time correlated imaging," CICC 2009 Proceedings of the IEEE 2009 Custom Integrated Circuits Conference. IEEE Society, San Jose, U.S.A, pp. 77-80, CICC 2009, San Jose, U.S.A., Sep. 13, 2009. https://doi.org/doi:10.1109/CICC.2009.5280890.
Takai, et al., "Single-Photon Avalanche Diode with Enhanced NIR-Sensitivity for Automotive LIDAR Systems," Sensors, 2016, 16(4): 459, pp. 1-9 (Year: 2016).
Torricelli, et al., "Time domain functional NIRS imaging for human brain mapping," NeuroImage 85, 28-50 (2014).
Wabnitz, et al., "Depth-selective data analysis for time-domain fNIRS: moments vs. time windows," Biomed. Opt. Express 11 (8), 4224 (2020).
Wabnitz, et al., "Performance assessment of time-domain optical brain imagers, part 1: basic instrumental performance protocol," Journal of Biomedical Optics 19(8), 086010 (Aug. 2014).
Wabnitz, et al., "Performance assessment of time-domain optical brain imagers, part 2: nEUROPt protocol," Journal of Biomedical Optics 19(8), 086012 (Aug. 2014).
Wojtkiewicz, et al., "Self-calibrating time-resolved near infrared spectroscopy," Biomed. Opt. Express 10(5), 2657 (2019).
Zhang, et al., "A CMOS SPAD Imager with Collision Detection and 128 Dynamically Reallocating TDCs for Single-Photon Counting and 3D Time-of-Flight Imaging," Sensors (Basel, Switzerland), 18(11), 4016. doi:10.3390/s18114016.
Zucchelli, et al., "Method for the discrimination of superficial and deep absorption variations by time domain fNIRS," 2013 OSA Dec. 1, 2013 | vol. 4, No. 12 | DOI:10.1364/BOE.4.002893 | Biomedical Optics Express 2893.
International Search Report and Written Opinion received in International Application No. PCT/2020/027537, dated Sep. 7, 2020.
International Search Report and Written Opinion received in international Application No. PCT/2020/028820, dated Aug. 26, 2020.
International Search Report and Written Opinion received in International Application No. PCT/US20/34062, dated Aug. 26, 2020.
International Search Report and Written Opinion received in International Application No. PCT/US2018/058580, dated Feb. 12, 2019.
International Search Report and Written Opinion received in International Application No. PCT/US2018/062777, dated Feb. 13, 2019.
International Search Report and Written Opinion received in International Application No. PCT/US2019/019317, dated May 28, 2019.
Non-Final Office Action received in U.S. Appl. No. 16/177,351, dated Apr. 1, 2019.
Non-Final Office Action received in U.S. Appl. No. 16/283,730, dated May 16, 2019.
Non-Final Office Action received in U.S. Appl. No. 16/370,991, dated Feb. 10, 2020.
Non-Final Office Action received in U.S. Appl. No. 16/567,360, dated Feb. 25, 2020.
Non-Final Office Action received in U.S. Appl. No. 16/544,850, dated Jun. 25, 2020.
Non-Final Office Action received in U.S. Appl. No. 16/856,524, dated Dec. 1, 2020.
Partial Search Report received in International Application No. PCT/2020/028820, dated Jul. 1, 2020.
Partial Search Report received in International Application No. PCT/US2020/027537, dated Jul. 17, 2020.

\* cited by examiner

US 11,515,014 B2

METHODS AND SYSTEMS FOR INITIATING AND CONDUCTING A CUSTOMIZED COMPUTER-ENABLED BRAIN RESEARCH STUDY

RELATED APPLICATIONS

The present application claims priority under 35 U.S.C. § 119(e) to U.S. Provisional Patent Application No. 63/126,933, filed on Dec. 17, 2020, and to U.S. Provisional Patent Application No. 62/979,852, filed on Feb. 21, 2020. These applications are incorporated herein by reference in their respective entireties.

BACKGROUND INFORMATION

Since the inception of technologies capable of imaging and analyzing the human brain, brain research has been performed to gain insights into human physiology, psychology, and behavior. While efforts of brain researchers have yielded great advances in the past, brain research has traditionally been a painstaking and difficult undertaking. For example, a conventional method of conducting a brain research study may begin with a brain research team interviewing a group of potential subjects to determine a sub-group of subjects that fits certain criteria for a particular brain research study that the researchers wish to conduct. Each subject in the sub-group may then be separately tested and analyzed using expensive and sensitive equipment (e.g., magnetic resonance imaging ("MRI") machines, functional MRI ("fMRI") machines, electroencephalography ("EEG") equipment, etc.) under supervision of the research team until sufficient data can be collected to draw conclusions and/or otherwise meet objectives of the study. This process can be laborious, time consuming, expensive, and difficult to coordinate.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
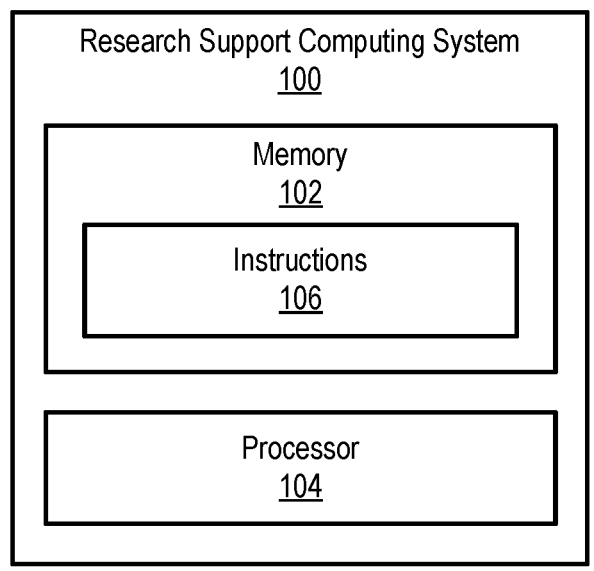
FIG. 1 shows an illustrative research support computing system for initiating and conducting a computer-enabled brain research study according to principles described herein.

Methods and systems for initiating and conducting a customized computer-enabled brain research study are described herein. As mentioned above, conventional brain research studies may require considerable legwork to be done by one or more researchers on a research team. For example, after objectives and parameters for a particular brain research study have been identified by the research team, team members may conduct one or more rounds of interviews of potential research subjects to identify a research subject group for the study. Selected research subjects may then meet with researchers during one or more sessions so that complex and expensive equipment may be used to examine the subjects' brains under preconfigured circumstances and under the direct supervision of the research team. Finally, data may be manually gathered and compiled by the research team in order to process the data and determine results and/or conclusions of the research study.

As will be described in more detail below, computer-enabled brain research studies described herein employ computing and networking technologies, as well as new and more accessible types of brain interface systems, to improve and streamline various aspects of this conventional process. For example, methods and systems described herein for initiating and conducting a computer-enabled brain research study may bypass the entire interview process of potential research subjects by maintaining subject data representative of respective sets of relevant attributes for a plurality of research subjects of a potential subject pool for potential research studies. As such, after defining parameters for a research study and setting desirable criteria for research subjects of the study, researchers may abstain from most or all of the interviewing and other research subject selection work that would conventionally be required. Additionally, once a research subject group has been automatically formed by research support computing systems described herein, these systems may interoperate with respective brain interface systems associated with each research subject (e.g., portable and relatively inexpensive brain interface systems that the research subjects may operate without direct supervision in their homes, classrooms, workplaces, laboratories, etc.) to thereby collect and, in certain examples, perform processing operations on the data. Raw and/or processed results data may then be provided back to the researchers who, instead of being burdened with the details of managing research subjects and data processing details, may be freed up to further analyze the results data, write up the research results, and/or move forward with follow-up studies and/or other research.

Accordingly, methods and systems described herein may allow for custom research studies (e.g., experiments, observations, etc.) to be performed exactly in accordance with parameters and criteria that a researcher desires, but with relatively little work or oversight by the researcher after the objectives and parameters of the study have been designed. These methods and systems provide support for real-time subject selection and regulatory approval (e.g., from a pool of prescreened and/or pre-analyzed remote test subjects), time coded feature data acquisition, and data sharing analysis. As will be described in more detail below, research support computing systems described herein may provide a computer interface (e.g., possibly including elements such as a graphical user interface, an application programming interface ("API"), a full software development kit ("SDK"), etc.) by way of which a client device used by a researcher may order and direct the creation of a research subject group, the conducting of research tasks by selected research subjects, the processing and analysis of results data, sharing and publishing the study results, and so forth.

Various advantages and benefits may arise from methods and systems described herein for initiating and conducting a computer-enabled brain research study. Several of these benefits have already been mentioned or made apparent above. For instance, various types of work involved in putting together a research subject group (e.g., posting flyers requesting research subjects, analyzing questionnaires filled out by potential research subjects, interviewing or otherwise screening potential research subjects, etc.), applying for regulatory approval to perform a particular brain research study, overseeing data acquisition (e.g., overseeing complex MRI or fMRI machines while individual research subjects are analyzed, etc.), and so forth, may all be automatically performed or significantly facilitated by research support computing systems described herein.

Although brain research studies are described herein, it will also be appreciated that other types of studies directed to other functions of a human subject (e.g., cardiac functions, vision functions, hearing functions, body movements, etc.) may also be conducted using methods and systems described herein. For instance, these other types of studies may be conducted together with any of the brain research studies described herein, or may be conducted independently of any research study associated with the brain.

Additional advantages and benefits may not only improve the efficiency of previous research approaches, but may further improve the research itself and technologies used to perform the research. For example, instead of being limited to research subjects that meet logistical geographic requirements (e.g., research subjects located within driving distance of a research clinic where research sessions are to be performed, etc.), remote research subjects located anywhere in the world may be included in a study since novel and relatively accessible brain interface systems described herein may allow research subjects to participate from home, from a classroom, or from various other locations other than research clinics. This may, in turn, allow for research studies that capture wider demographics and more accurate population sampling than may be possible or reasonably achievable when geographic limitations exist.

Another example benefit is that research data may be accessed (e.g., viewed by the research team) and processed in real time (e.g., immediately as the research data is acquired). Certain data processing features of brain interface systems described herein may even support experimental analysis right at the sensor level (e.g., by devices near the subject's scalp as brain measurements are being recorded). Additionally, along with accessing and processing the research data, systems and methods described herein may provide data sharing capabilities that allow researchers to share the research data with other researchers (e.g., in real time or for subsequent studies to take place in the future), as well as to likewise access and make use of research data from current and/or prior research studies having similar parameters, criteria, and/or objectives. In this way, large and standardized research datasets may be compiled, used, and studied by researchers to examine a diverse set of questions across academia and industry.

Measurement systems and technologies that can be used to enable population-level studies, e.g., brain studies, cardiac studies, drug studies, health/wellness studies, other medical studies, user exercise/movement studies, sleep studies, meditation studies, product or consumer studies, or the like or any combination thereof, particularly the studies which utilize a relatively large population of participants/subjects, are described more fully in U.S. Provisional Patent Application Ser. No. 63/136,093, filed Jan. 11, 2021, and U.S. Provisional Application No. 63/076,015, filed Sep. 9, 2020, which applications are incorporated herein by reference in their entirety.

Various specific embodiments will now be described in detail with reference to the figures. It will be understood that the specific embodiments described below are provided as non-limiting examples of how various novel and inventive principles may be applied in various situations. Additionally, it will be understood that other examples not explicitly described herein may also be captured by the scope of the claims set forth below. Methods and systems described herein for initiating and conducting a computer-enabled brain research study may provide any of the benefits mentioned above, as well as various additional and/or alternative benefits that will be described and/or made apparent below.

FIG. 1 shows an illustrative research support computing system 100 ("system 100") for initiating and conducting a computer-enabled brain research study in accordance with principles described herein. System 100 may be implemented by computer resources such as server systems or other computing devices that include processors, memory facilities, storage facilities, communication interfaces, and so forth. For example, system 100 may be implemented by computing systems such as local computing systems operated by a user, distributed computing systems operated by a data services provider (e.g., multi-access cloud servers, multi-access edge computing servers, etc.), or any other suitable computing system or systems.

As shown, system 100 may include, without limitation, a memory 102 and a processor 104 selectively and communicatively coupled to one another. Memory 102 and processor 104 may each include or be implemented by computer hardware that is configured to store and/or execute computer software. Various other components of computer hardware and/or software not explicitly shown in FIG. 1 may also be included within system 100. In some examples, memory 102 and processor 104 may be distributed between multiple devices and/or multiple locations as may serve a particular implementation.

Memory 102 may store and/or otherwise maintain executable data used by processor 104 to perform any of the functionality described herein. For example, memory 102 may store instructions 106 that may be executed by processor 104. Memory 102 may be implemented by one or more memory or storage devices, including any memory or storage devices described herein, that are configured to store data in a transitory or non-transitory manner. Instructions 106 may be executed by processor 104 to cause system 100 to perform any of the functionality described herein. Instructions 106 may be implemented by any suitable application, software, script, code, and/or other executable data instance. Additionally, memory 102 may also maintain any other data accessed, managed, used, and/or transmitted by processor 104 in a particular implementation.

Processor 104 may be implemented by one or more computer processing devices, including general purpose processors (e.g., central processing units ("CPUs"), graphics processing units ("GPUs"), microprocessors, etc.), special purpose processors (e.g., application-specific integrated circuits ("ASICs"), field-programmable gate arrays ("FPGAs"), etc.), or the like. Using processor 104 (e.g., when processor 104 is directed to perform operations represented by instructions 106 stored in memory 102), system 100 may perform functions associated with initiating and conducting a computer-enabled brain research study as described herein and/or as may serve a particular implementation.

Figure 2:
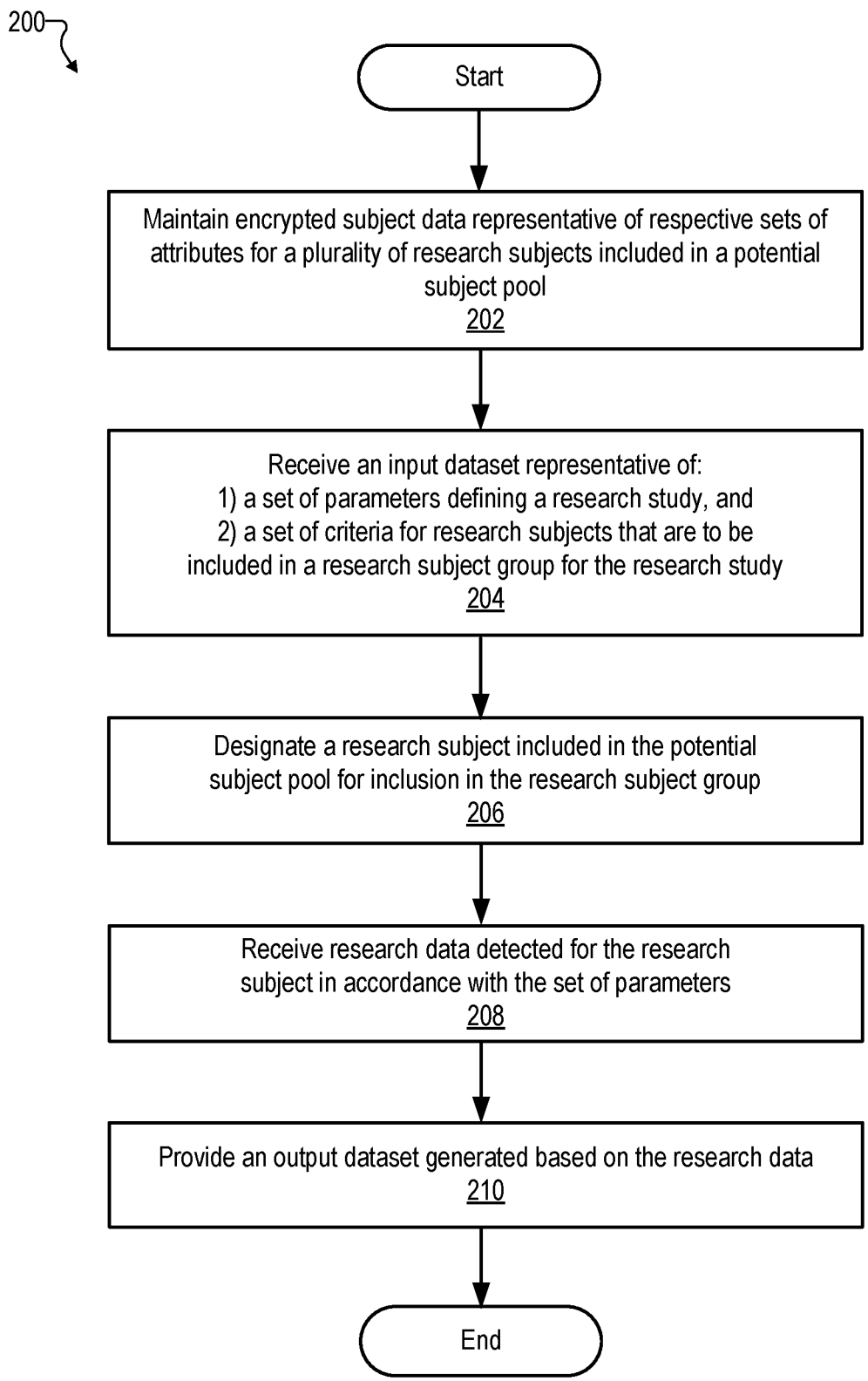
FIG. 2 shows an illustrative method for initiating and conducting a computer-enabled brain research study according to principles described herein.

As one example of functionality that processor 104 may perform, FIG. 2 shows an illustrative method 200 for initiating and conducting a computer-enabled brain research study in accordance with principles described herein. While FIG. 2 shows illustrative operations according to one embodiment, other embodiments may omit, add to, reorder, and/or modify any of the operations shown in FIG. 2. In some examples, multiple operations shown in FIG. 2 or described in relation to FIG. 2 may be performed concurrently (e.g., in parallel) with one another, rather than being performed sequentially as illustrated and/or described. One or more of the operations shown in FIG. 2 may be performed by a research support computing system such as system 100 and/or any implementation thereof.

In some examples, the operations of FIG. 2 may be performed in real time so as to provide, receive, process, and/or use data described herein immediately as the data is generated, updated, changed, exchanged, or otherwise becomes available. Moreover, certain operations described herein may involve real-time data, real-time representations, real-time conditions, and/or other real-time circumstances. As used herein, "real time" will be understood to relate to data processing and/or other actions that are performed immediately, as well as conditions and/or circumstances that are accounted for as they exist in the moment when the processing or other actions are performed. For example, a real-time operation may refer to an operation that is performed immediately and without undue delay, even if it is not possible for there to be absolutely zero delay. Similarly, real-time data, real-time representations, real-time conditions, and so forth, will be understood to refer to data, representations, and conditions that relate to a present moment in time or a moment in time when decisions are being made and operations are being performed (e.g., even if after a short delay), such that the data, representations, conditions, and so forth are temporally relevant to the decisions being made and/or the operations being performed.

Each of operations 202-210 of method 200 will now be described in more detail as the operations may be performed by system 100 (e.g., by processor 104 as processor 104 executes instructions 106 stored in memory 102).

At operation 202, system 100 may maintain subject data representative of respective sets of attributes for a plurality of research subjects included in a potential subject pool for potential research studies. For example, the potential subject pool may include a relatively large number of people (e.g., more people than may be needed for any one particular research study) who, for any of various reasons, are considered to be viable candidates for participating in research studies that researchers may wish to conduct. As one example of what may make the people in the potential subject pool viable candidates, each person in the potential subject pool may have downloaded a mobile app associated with a research study service and used the mobile app to register with the service. For instance, the registration process may involve providing personal information indicating certain attributes of the person, filling out a questionnaire that may serve to gather attribute data for various types of research studies, signing waivers associated with particular types of research studies, and so forth. The acquired personal information of the person may then be encrypted and/or encoded per regulatory and/or privacy government protocols designed for protecting and storing personal data.

All of the information provided by registered participants in this way or in other suitable ways may be maintained as the subject data by system 100 (e.g., within memory 102 or another suitable data store associated with system 100) by intaking, organizing, storing, providing, and/or otherwise managing the data in any manner as may serve a particular implementation. Within the maintained subject data, a respective set of attributes indicative of demographic information, preferences, lifestyle characteristics, responses to questions, and so forth may be stored for each person included in the potential research subject pool. As will be described in more detail below, this subject data may be used by system 100 to automatically generate and set up a research subject group that comports with criteria defined by a researcher using system 100 to facilitate research study initiation.

At operation 204, system 100 may receive an input dataset from a client device. For example, the client device may be associated with (e.g., used by) a user such as a member of a research team who desires to conduct a particular research study. As such, the client device may be physically remote from system 100, which may be implemented by a server configured to serve various client devices of various users from a centralized location, and system 100 may perform the receiving of the input data by way of a network that interconnects the research support computing system and the client device. Additionally, in order to facilitate the client device in providing proper data in the input dataset, the input dataset may be received by way of a computer interface that is provided by system 100. For instance, the computer interface may include a graphical user interface, an API, an SDK, or any other interfacing or presentation tools configured to facilitate users (e.g., researchers) in defining and providing suitable information in the input dataset to allow system 100 to provide research support services described herein.

The input dataset received by system 100 at operation 204 may include any of various types of data used to define parameters and/or objectives for a research study and its participants as may serve a particular implementation. For example, as noted at operation 204 in FIG. 2, the input dataset may include a set of parameters defining a research study to be conducted with respect to a research subject group, as well as, in certain examples, a set of criteria for research subjects that are to be included in the research subject group.

The set of parameters may define any aspects of the research study as may serve a particular implementation. For instance, as will be described in more detail below, the set of parameters may define an experiment design (e.g., including a duration of each monitoring session, a number of sessions to be monitored per research subject, an environment within which the research subjects are to be located during each session, a description of measurements that are to be monitored and recorded, equipment that is to be used to perform brain monitoring during each session, etc.), a trial type (e.g., a sample size or total number of research subjects, a number of cohorts into which the research subject group is to be divided, a trial methodology, one or more endpoints that the trial may attempt to isolate or identify, etc.), and/or any other parameters as may be described herein or as may serve a particular implementation.

The set of criteria for research subjects to be included in the research subject group may include criteria associated with any demographic attributes, personal attributes, skills-related or experience-related attributes (e.g., education, employment, etc.), or other attributes or characteristics of research subjects desired for the research subject group. For instance, as will be described in more detail below, the set of criteria may include demographic criteria such as desired genders, age ranges, ethnicities, nationalities, geographies of residence, or other such characteristics of potential research subjects for potential research studies. Additionally, skills-related or experience-related criteria included in the set of criteria may relate to particular levels of educational attainment, particular schools or types of schools attended, particular industries of current or past employment, and so forth. Other research subject criteria (e.g., including custom criteria defined by a particular researcher rather than provided as an option by system 100) may relate to other attributes or characteristics desired for research subjects to be selected for the research subject group (e.g., lifestyle choices of potential research subjects, family details of potential research subjects, habits of potential research subjects, the way potential research subjects spend their time, etc.).

At operation 206, system 100 may designate one or more research subjects included in the potential subject pool for inclusion in the research subject group. For example, the designation of research subjects for inclusion in the research subject group at operation 206 may be performed based on the subject data maintained at operation 202, as well as the set of criteria received in the input dataset at operation 204. More particularly, the subject data that has already been collected and organized at operation 202 may be analyzed against the set of research subject criteria received for a particular research study at operation 204 to determine which potential research subjects from the potential subject pool would be suitable and/or most ideal for what is desired for a particular research study. As potential candidates are filtered and identified in this way, system 100 may designate suitable research subjects for inclusion in the research subject group (e.g., the research subjects determined to best meet the set of criteria provided by the client device in the input dataset).

At operation 208, system 100 may receive research data detected for the one or more research subjects designated at operation 206 for inclusion in the research subject group. For example, after creating the research subject group by way of the designations of operation 206, each designated research subject of the research subject group may be directed (e.g., by system 100, by instructions provided previously, etc.) to perform particular tasks using particular equipment configured to monitor and record research data (e.g., brain wave patterns or other signals produced by the brains of the research subject, etc.). Research data may be detected in accordance with the set of parameters defining the research study received in the input dataset at operation 204. As such, the research data may represent each research subject as the research subject engages in particular monitoring or testing sessions of particular types indicated by the experiment design, trial type, and/or other parameters defining the research study.

In certain examples, system 100 may receive the research data detected for the research subjects from respective brain interface systems used by each of the research subjects. For example, these brain interface systems may be highly accessible systems (e.g., system that are low cost, portable, safe, straightforward to operate with minimal training, etc.) that research subjects may use remotely from system 100 such as from their own homes, classrooms, workplaces, or the like. Examples of such brain interface systems will be described in more detail below, as well as different illustrative geographic configurations of the research subjects, brain interface systems, and system 100.

At operation 210, system 100 may provide an output dataset generated based on the research data received at operation 208 (i.e., the research detected for each of the research subjects of the research subject group in accordance with the set of parameters defining the research study). As will be described in more detail below, the output dataset may be related to the received research data (e.g., raw or unprocessed research data that is detected by the brain interface systems) in any suitable manner. For instance, in certain examples, raw research data indicative of what the brain interface systems detected may be provided directly to allow the client device or other systems associated with the client device (e.g., and likewise operated by the research team) to process the raw research data to organize, analyze, and identify research conclusions based on the data. In other examples, system 100 may perform certain processing on the raw research data prior to providing the output dataset at operation 210. As such, in these examples, the output data may not provide the raw research data but rather may provide information derived from the research data (e.g., research results data) that allows the client device to forego at least some of the additional processing that might otherwise be performed in conventional examples.

Figure 3:
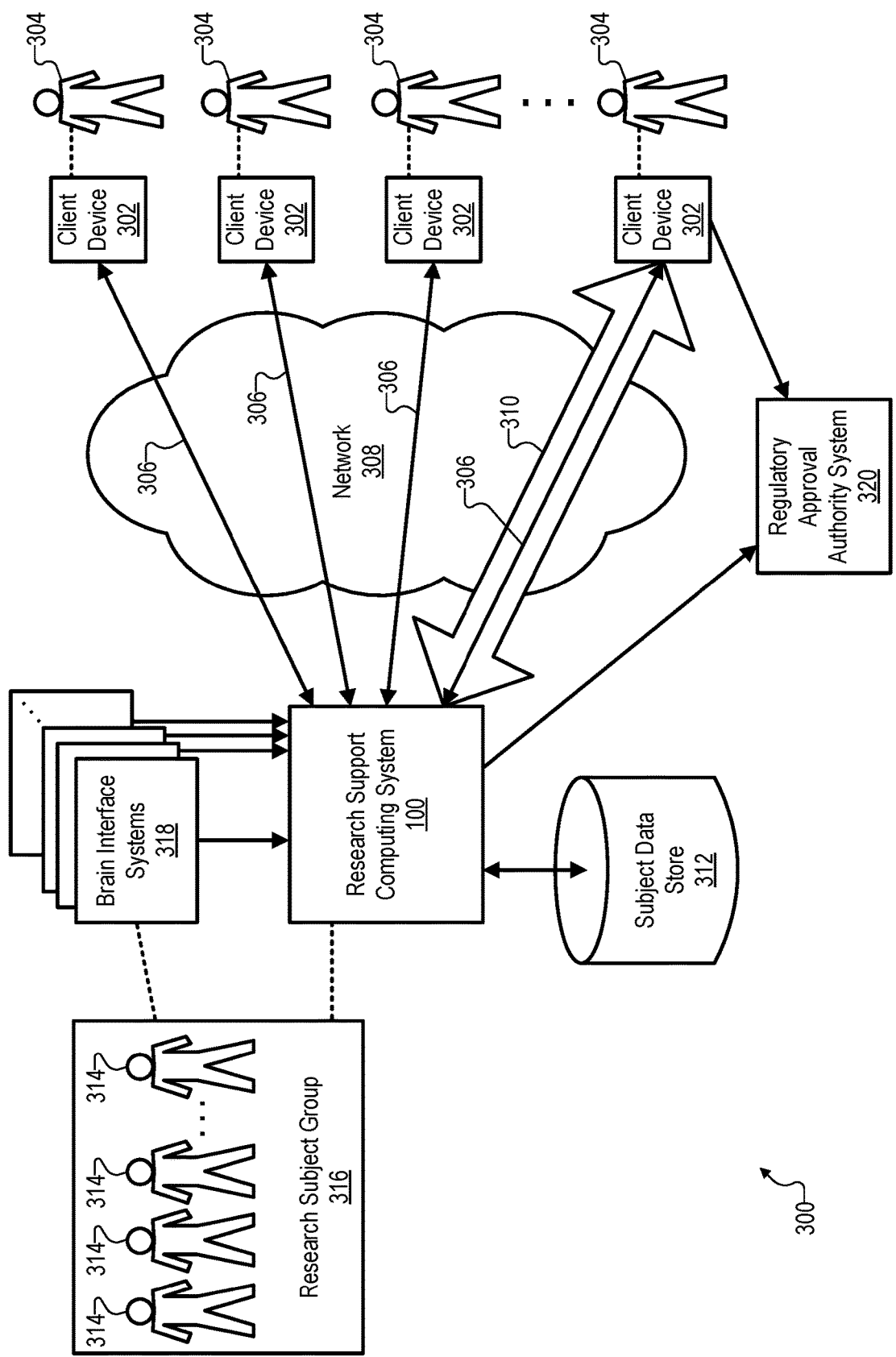
FIG. 3 shows an illustrative configuration within which the research support computing system of FIG. 1 operates according to principles described herein.

FIG. 3 shows an illustrative configuration 300 within which system 100 may operate in certain implementations and in accordance with principles described herein. As shown in FIG. 3, system 100 may be communicatively coupled with a plurality of client devices 302 that are each operated by a respective user 304. Communications 306 between system 100 and each client device 302 are shown to be carried out by way of a network 308 that interconnects system 100 and client devices 302. Moreover, a computer interface 310 represented by a large arrow for a particular one of communications 306 between system 100 and a particular one of client devices 302 is depicted to illustrate that system 100 may provide a suitable computer interface (e.g., a graphical user interface, an API, an SDK, etc.) and may communicate with certain client devices 302 (e.g., including receiving input datasets, providing output datasets, etc.) by way of the computer interface.

System 100 is further shown to be communicatively coupled with a subject data store 312 that stores subject data for a potential subject pool (not explicitly shown in FIG. 3) from which system 100 designates a plurality of research subjects 314 for a research subject group 316. Subject data store 312 may also include encryption software required for encrypting and storing a subject's personal data and/or collected brain data in a manner comporting with regulatory and privacy government protocols, ethics organizations, and so forth. Respective brain interface systems 318 used by these research subjects 314 are communicatively coupled with system 100 to provide research data detected for different research subjects 314 to system 100. Additionally, system 100 is further shown to be communicatively coupled with a regulatory approval authority system 320 with which system 100 may communicate to automatically facilitate a regulatory approval process associated with research studies that users 304 may desire to carry out using system 100.

Each element of FIG. 3 will now be described in more detail as the elements interoperate with system 100 in the performance of research support computing methods such as method 200. FIGS. 4-11 will also be referenced in the following description to provide additional detail that may not be explicitly illustrated in the relatively high-level view provided by FIG. 3.

Client devices 302 may be implemented by any suitable types of computing devices as may be employed by users 304 to perform operations described herein. For instance, client devices 302 may be implemented by computing devices capable of network communications over network 308 (e.g., particularly those involving computer interface 310 provided by system 100), capable of generating and transmitting input datasets to system 100, capable of capturing parameters and criteria desired by users 304 to define desired characteristics of potential research studies, capable of receiving and (in certain examples) further processing research data transmitted by system 100, and so forth. To this end, client devices 302 may be implemented by general purpose personal computers (e.g., laptop computers, desktop computers, etc.), mobile devices (e.g., smartphones, tablet devices, etc.), special-purpose computing systems designed to augment and/or facilitate research-related functionality, or other suitable computing systems executing software (e.g., application-based or browser-based software) that is configured to enable or facilitate operations described herein.

Users 304 of client device 302 may represent researchers (i.e., members of brain research teams) or others who desire to leverage system 100 to initiate and conduct computer-enabled research studies in the ways described herein. As has been described, rather than having to perform the conventional legwork to initiate and run brain research studies, researchers may choose to access system 100 by way of client devices 302 to take advantage of features and benefits of computer-enabled research studies described herein.

Network 308 may be employed in configuration 300 to interconnect client devices 302 with each other and/or with system 100. To this end, network 308 may include any network elements and/or characteristics as may serve a particular implementation. For example, network 308 may include elements of a provider-specific wired or wireless communications network (e.g., a cellular network used for mobile phone and data communications, a 5G network or network of another suitable technology generation, a cable or satellite carrier network, a mobile telephone network, etc.) operated and/or managed by a provider entity such as a mobile network operator (e.g., a wireless service provider, a wireless carrier, a cellular company, etc.). Additionally or alternatively, network 308 may include elements of various interconnected networks that are outside of any provider network and outside the control of any provider of such a provider network. Elements of the Internet, a wide area network, a content delivery network, and/or any other suitable network or networks are examples of other elements that may be included within network 308. Any of these provider or non-provider networks or network elements may provide data delivery between system 100 and client devices 302.

Communications 306 between system 100 and each of client devices 302 are shown to be two-way communications that are carried by network 308 and, at least in certain examples, are established by way of a computer interface provided by system 100, such as computer interface 310.

Figure 4:
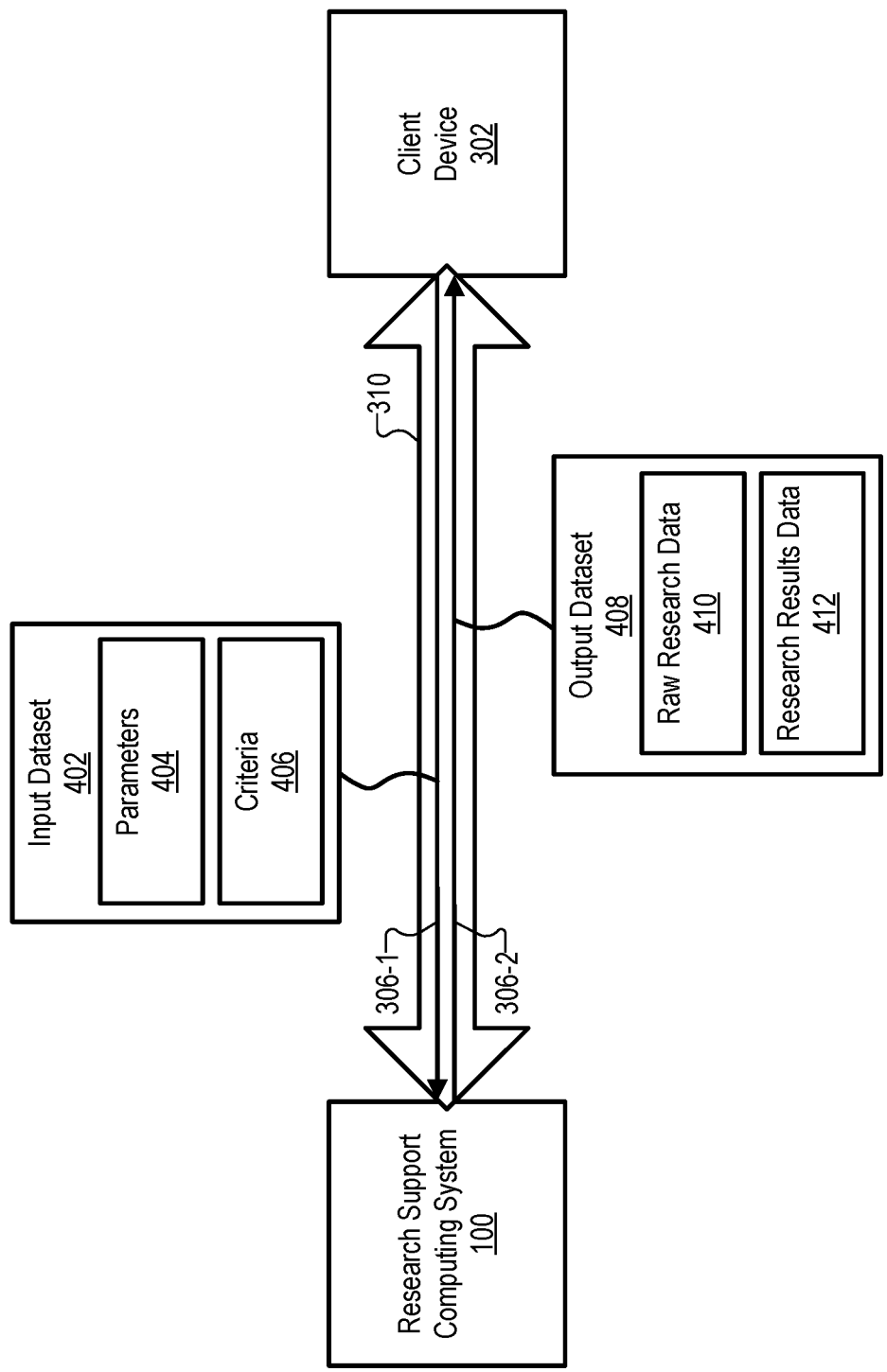
FIG. 4 shows illustrative data communicated between the research support computing system and a client device in the configuration of FIG. 3 according to principles described herein.

To illustrate, FIG. 4 shows an example of data that may be communicated between system 100 and a particular client device 302 in configuration 300. Specifically, FIG. 4 shows that a communication 306 between system 100 and a client device 302 may be broken out into a separate input communication 306-1 and an output communication 306-2, either or both of which may be communicated by way of computer interface 310. Input communication 306-1 is shown to be a communication from client device 302 to system 100 that includes an input dataset 402 that may include a set of parameters 404, a set of criteria 406, and/or any other data as may serve a particular implementation. In contrast, output communication 306-2 is shown in FIG. 4 to be a communication from system 100 to client device 302 that includes an output dataset 408 that may include raw research data 410, research results data 412, and/or any other data as may serve a particular implementation. Input dataset 402 will now be described in more detail, while output dataset 408 will be described below after the process of selecting a research subject group and collecting and processing research data has been described with respect to FIGS. 5-10.

Input dataset 402 may include a research support request from client device 302 to system 100, as well as various types of data in support of that request. For example, if the research support request aims to initiate and conduct a computer-enabled brain research study in accordance with principles described herein, data such as a set of parameters 404 that define the brain research study and a set of criteria 406 for research subjects that are to be included in the research subject group may be included.

The set of parameters 404 may define any aspects of the brain research study in any manner as may serve a particular implementation. For example, parameters 404 may include parameters for the research study that set forth how many research subjects or data sets are to be tested as part of the study, the number of times each subject should be tested, the duration of each test and/or of the entire study, the environment in which subjects should be located and/or activities in which the subjects should be engaged during testing sessions (e.g., driving in a car, performing a task on a computer or device, listening to music, learning or teaching in a classroom, eating a meal, exercising, etc.), peripheral equipment that is to be involved in the testing (e.g., pulse monitors, etc.), specific tests or characteristics that are to be monitored, specific variables that are to be controlled for, objectives of the research study (e.g., to identify cognitive anomalies that may occur after many hours of driving or in unique driving scenarios, etc.), and/or any other parameters described herein or as may serve a particular implementation.

The set of criteria 406 may define any characteristics of potential research subjects that would be desirable or undesirable for the objectives of the research study. For instance, if the research study aims to reveal how neural patterns experienced during driving activities evolve with age for women, criteria 406 may indicate that women of driving age are to be included in the research subject group, that the age of the women should follow a particular distribution that guarantees data along the spectrum of different ages, that men and girls not yet old enough to drive are to be excluded from the research subject group, that women who do not drive regularly may be sub-optimal research subjects, and so forth. Any of these types of criteria and/or other criteria described herein may serve as criteria 406 provided in input dataset 402 to enable system 100 to put together a highly optimized research subject group.

Computer interface 310 may be provided by system 100 to facilitate the providing and receiving of parameters 404 and criteria 406 of input dataset 402. For example, computational structure, input rules, data definitions, and/or other aspects of computer interface 310 may help system 100 efficiently input the necessary data from users 304 and ensure that input dataset 402 includes suitable data, in an expected and preconfigured form, to allow system 100 to perform the research support operations described herein.

In certain implementations, the computer interface 310 provided by system 100 may include an API that defines functions, data types, and so forth, to allow a programming-savvy user 304 to write code allowing his or her client device 302 to directly interface with system 100 and its resources (e.g., subject data store 312, the communicative links of system 100 to brain interface systems 318 and/or regulatory approval authority system 320, etc.). The API may allow a user 304 not only to interface with system 100 for purposes of providing input direction defining the research study, but also for directing system 100 to process research data and/or results data in particular ways and for providing output dataset 408 in accordance with particular parameters. In certain examples, computer interface 310 may include or be implemented by an SDK in addition to or as an alternative to the API described above. For example, a text-based and/or graphics-based editor may be provided as part of an SDK to facilitate user 304 in providing instructions to system 100 and/or receiving resultant data back from system 100 in any suitable manner. In certain of these examples, client device 302 may avoid running code or performing data analysis since system 100 may perform this functionality (in accordance with direction provided by way of the API and/or SDK) instead.

In some implementations, the computer interface 310 provided by system 100 may include a graphical user interface in addition or as an alternative to text-based interfaces associated with APIs and/or SDKs described above. For instance, an application-based or browser-based graphical user interface may provide options that users 304 (e.g., users who may not be particularly programming savvy or whose needs do not require the flexibility and customizability of an API-based interface) may conveniently fill in and select to efficiently define parameters 404 and/or criteria 406 for a desired research study. A graphical user interface implementing or included within computer interface 310 may include various graphical elements such as drop-down boxes, check boxes, text fields, buttons, switches, number fields, text fields, and so forth. For example, in one particular embodiment, the graphical user interface may include one or more graphical elements configured for use by user 304 of client device 302 to input one or more parameters 404, as well as one or more additional graphical elements configured for use by user 304 of client device 302 to input one or more criteria 406 of the set of criteria for the research subjects that are to be included in the research subject group.

Figure 5:
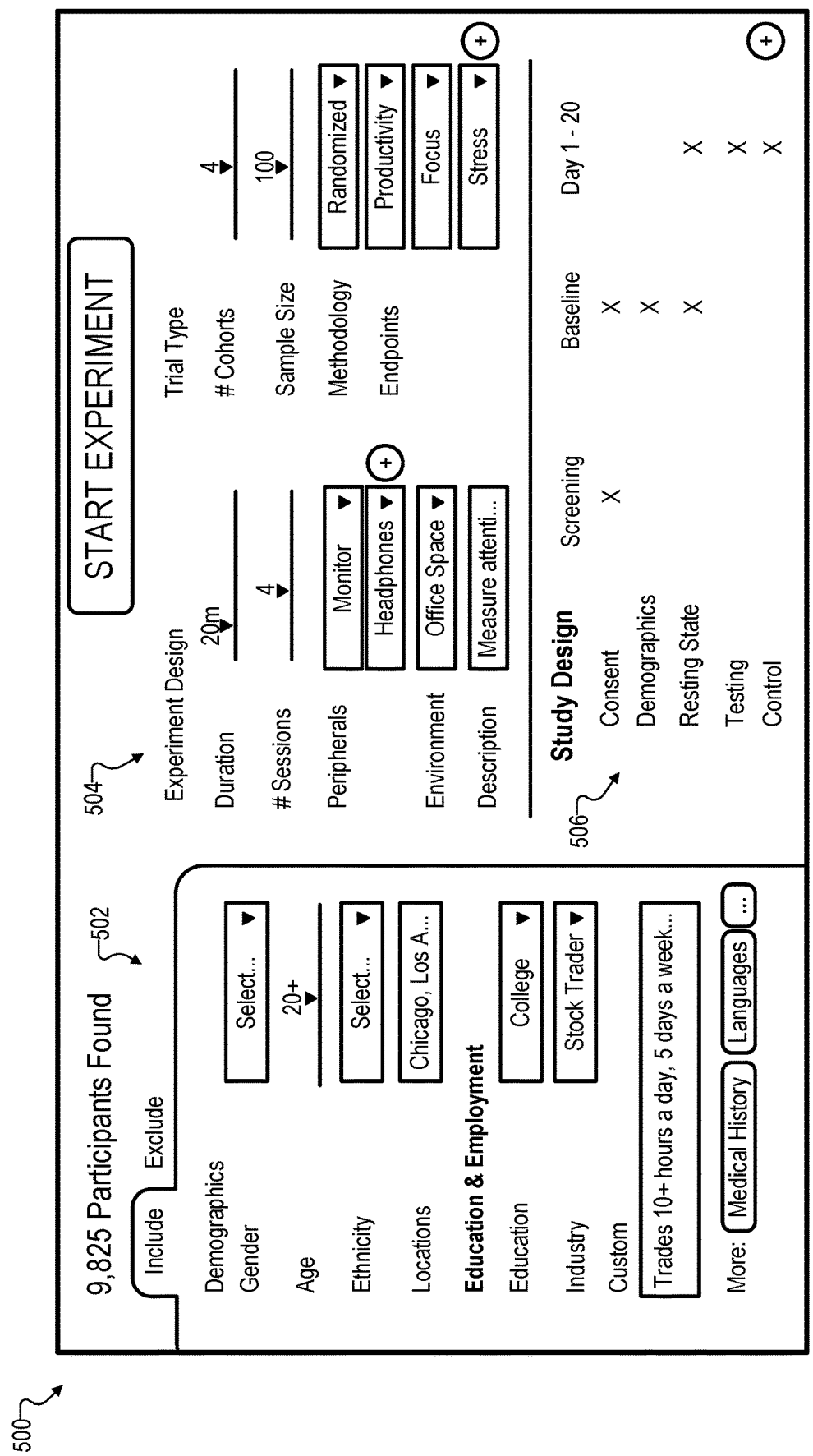
FIG. 5 shows an illustrative graphical user interface included within a computer interface provided by the research support computing system to a client device according to principles described herein.

To illustrate, FIG. 5 shows an example graphical user interface 500 included within an example computer interface 310 provided by system 100 to client devices 302 in accordance with principles described herein. As shown and as will be described in more detail in certain examples below, various graphical elements configured to facilitate user input and/or output may be included within graphical user interface 500. While certain example elements are illustrated in FIG. 5, it will be understood that any of the illustrated graphical elements or any other graphical elements mentioned herein or of use in certain examples may be included in a particular implementation of graphical user interface 500.

As shown, one section of graphical user interface 500 is a research subject criteria interface 502 that allows a user to input subject attributes that are to be included (as entered using the "Include" tab depicted in FIG. 5) and subject attributes that are to be excluded (as entered using an "Exclude" tab not currently selected in the depiction of FIG. 5). For example, if particular research aims to study brain functions of non-professional drivers during driving activities, a graphical element (e.g., a number field, a drop-down menu with selectable options, etc.) associated with research subject ages that are to be included in the research subject group ("Age") may define an attribute that is to characterize each research subject designated for inclusion in the research subject group (e.g., that the subject is of driving age, 16 or older). At the same time, another graphical element on the "Exclude" tab (not shown) may define an additional attribute that is not to characterize any research subject designated for inclusion in the research subject group. For instance, such a graphical element may be associated with industries in which research subjects are not to be employed (e.g., potential research subjects employed in the transportation or trucking industries are to be excluded for the driving research example above, etc.).

Another section of graphical user interface 500 is an experiment parameter interface 504 that allows a user to input and/or update and refine parameters defining various aspects of the research study that is to be conducted. For example, as shown, experiment parameter interface 504 may include inputs defining an experimental design such as a duration of each test session that is to be performed for a given research subject, a number of sessions to be monitored for each research subject, peripheral equipment that is to be used or involved with the testing, an environment within which the research subjects are to be located during testing sessions, a description of measurements that are to be monitored and recorded, and/or any other experiment design parameters as may serve a particular implementation. Experiment parameter interface 504 may further include trial type inputs that define the overall experiment that is to be implemented according to the experiment design. For instance, as shown, experiment parameter interface 504 may facilitate input of parameters such as a number of cohorts into which the research subject group is to be divided, a sample size or total number of research subjects to be included in the research subject group, a trial methodology, one or more endpoints or other objectives of the experiment, and/or any other parameters as may be described herein or as may serve a particular implementation.

Along with facilitating the input of research subject criteria and experiment parameters using interfaces 502 and 504, graphical interface 500 may further include a graphical element configured to output, for display to the user 304 of the client device 302, status data indicative of a current status of the research study. Specifically, as shown, a status output interface 506 depicts certain task categories that must be completed as part of the research study and indications of the status of the study with respect to these task categories. For example, study design categories may relate to tasks such as gathering consent from research subjects, achieving certain demographics in the research subject group being put together, testing a resting state baseline for each research subject selected for the research subject group, testing each research subject while engaged in the desirable behavior being targeted by the research study (e.g., driving a vehicle in the driving example mentioned above), gathering control data that contextualizes the test data, and so forth. In certain examples, tasks may be performed repeatedly or in stages (e.g., a screening stage, a baseline stage, repeating for each of 20 sessions on 20 consecutive days, etc.). Such aspects may also be indicated by certain implementations of status output interface 506, as shown in FIG. 5.

Returning to FIG. 3, once system 100 has received an input dataset from a particular client device 302 (e.g., an input dataset such as input dataset 402 that is received by way of a computer interface 310 that includes an API or graphical user interface such as graphical user interface 500), system 100 may proceed with designating one or more research subjects 314 to be included in research subject group 316. For example, this designation process may involve analyzing the research subject criteria received from the client device 302 (e.g., research subject criteria 406) against subject data that is stored in subject data store 312 and is representative of respective sets of attributes for different research subjects included in a potential subject pool.

Subject data store 312 may be implemented as any suitable type of data storage facility such as a database, a data lake, or another suitable data storage structure. Additionally, while subject data store 312 is illustrated as being separate from system 100 in configuration 300, it will be understood that subject data store 312 may, in certain examples, be integrated into system 100 (e.g., implemented within non-transitory storage of memory 102, another storage resource not explicitly shown in FIG. 1, etc.) rather than being stored and accessed externally from system 100.

Figure 6:
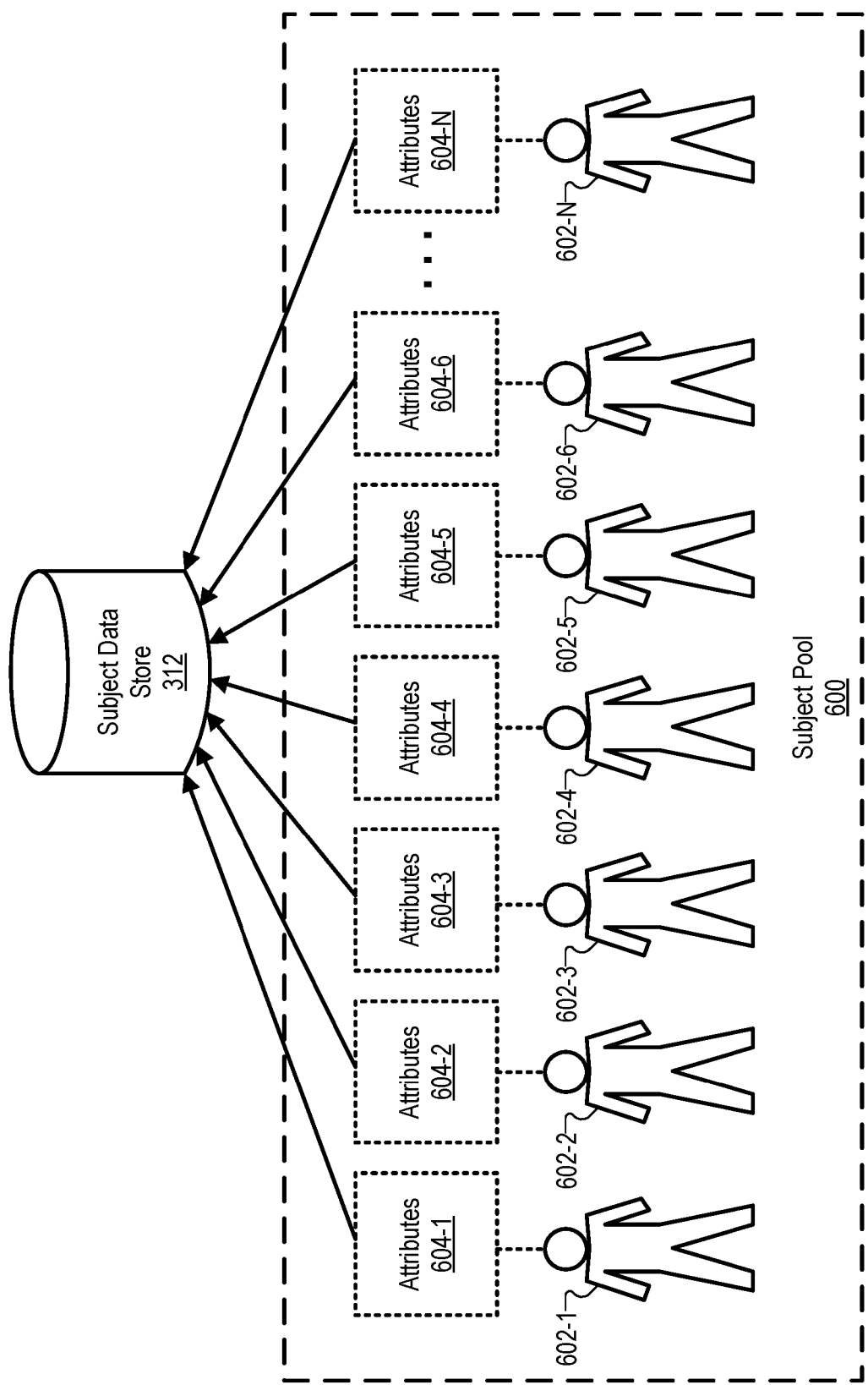
FIG. 6 shows an illustrative subject pool for which subject data is maintained by a research support computing system according to principles described herein.

To illustrate the process of designating research subjects 314 to form research subject group 316, FIG. 6 shows an illustrative subject pool 600 for which subject data is maintained by system 100. Specifically, as shown, system 100 maintains the subject data for subject pool 600 using subject data store 312 as a storage facility that, as mentioned above, may be integrated with or separate from system 100. In FIG. 6, a plurality of potential research subjects 602 (e.g., N potential research subjects 602-1 through 604-N in this example) is shown to each be associated with a respective set of attributes 604 (e.g., sets of attributes 604-1 through 604-N for the N research subjects included in subject pool 600 in this example). While a relatively small number of research subjects 602 are shown in FIG. 6 for the sake of clarity, it will be understood that subject pool 600 may include a large number of potential research subjects (e.g., the integer N representing the number of potential research subjects 602 may be in the hundreds or thousands or more in certain implementations).

Each research subject 602 included in subject pool 600 may be included for any suitable reason. For instance, in certain implementations, research subjects 602 in subject pool 600 may include research subjects 602 that are considered likely to have interest in participating in research studies (e.g., a student body of a particular university or a group of students studying a particular topic at the university, etc.). Additionally or alternatively, research subjects 602 in subject pool 600 may include people who have volunteered to be considered for research study opportunities, such as by downloading and registering a mobile application, or registering on a web site.

In certain examples, research subjects 602 within subject pool 600 may have access to brain interface system equipment that they can use, including any of the accessible and non-invasive brain interface system implementations described herein, and may already be trained regarding how to use the equipment. For example, the research subjects 602 may own a wearable brain interface system (e.g., purchased to allow them to sign up for research studies and earn cash for their participation) or may otherwise have access to a brain interface system (e.g., by leasing a system, by sharing a system with acquaintances or with strangers arranged by a resource sharing application, etc.). In other examples, research subjects 602 may not necessarily have access to their own brain interface system and may thus be provided with respective brain interface systems by an entity associated with system 100 or by members of a research team (e.g., a user 304). For instance, brain interface systems may be delivered by package delivery services directly to research subjects 602 in their homes or workplaces, or brain interface systems may be provided at a central location (e.g., a research clinic, a location of system 100, etc.) to which research subjects 602 travel for each testing or monitoring session in the research study.

The respective set of attributes 604 for each research subject 602 may include any suitable attributes (e.g., attributes relevant to the types of research subject criteria 406 that a user 304 has defined as described above), and may be provided by the research subject 602 in any suitable way and/or at any suitable time. For example, certain attributes may be indicated by a research subject 602 at a time of registration to be part of subject pool 600 (e.g., by answering questions and/or selecting options in a mobile application or website used to register). Other attributes may be indicated by the research subject 602 at a later time, such as in response to particular questions associated with a particular research study opportunity for which the research subject 602 desires to be considered. In either case, all of the attributes 604 that each research subject 602 provides may be stored and maintained by system 100 within subject data store 312 in any manner as may serve a particular implementation. Arrows from each set of attributes 604 to subject data store 312 illustrate this in FIG. 6.

Figure 7:
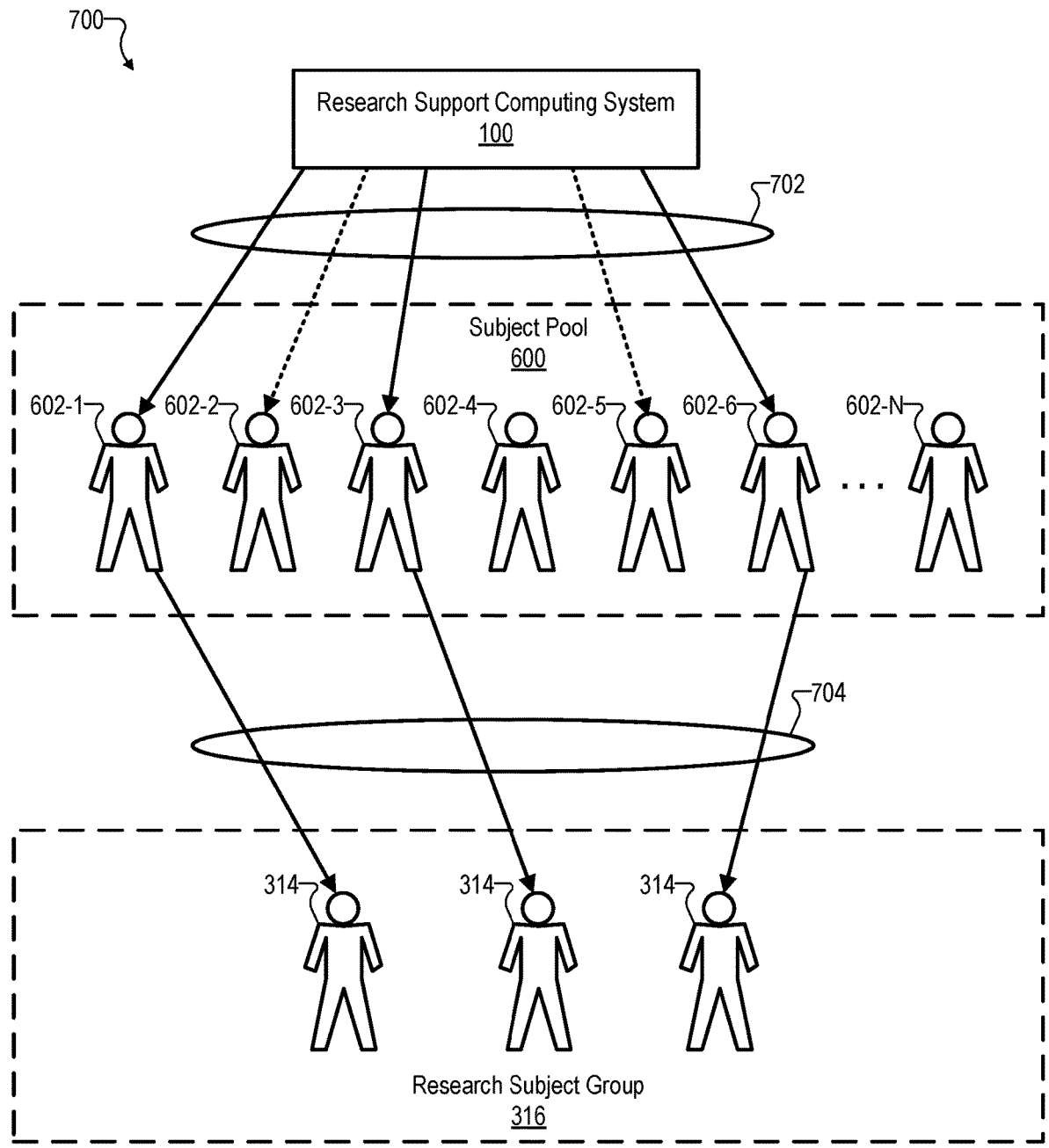
FIG. 7 shows an illustrative selection process by way of which a research support computing system generates a research subject group for a computer-enabled brain research study according to principles described herein.

FIG. 7 shows an illustrative selection process 700 by way of which system 100 may generates the research subject group 316 for a computer-enabled brain research study that is requested by a user 304. Depending on the nature of how subject pool 600 is constructed and the interest level of research subjects 602 included in the pool, different research subjects 602 may be prospectively designated for inclusion in research subject group 316 in different ways.

For instance, as one example, prospective designations 702 illustrated by solid arrows from system 100 to select research subjects 602 (i.e., research subjects 602-1, 602-3, and 602-6 in this example) illustrate a first way that system 100 may perform selection process 700. In this example, it is assumed that each research subject 602 in subject pool 600 is committed to participating in research studies for which they are designated, similar, for instance, to an employee who is presumed to be ready and willing to take on any assignment requested by his or her manager. Accordingly, as shown by final designations 704 illustrated by solid arrow from research subjects 602-1, 602-3, and 602-6 to designated research subjects 314, system 100 may determine ideal candidates from subject pool 600 and immediately designate them for inclusion in research subject group 316. More particularly, in this type of implementation, the designating of research subjects 314 for inclusion in research subject group 316 may include: 1) determining that a research subject 602 satisfies a certain set of criteria (e.g., defined by research subject criteria 406); 2) selecting, based on the determining that the research subject 602 satisfies the set of criteria, the research subject 602 for inclusion in research subject group 316; and 3) transmitting, based on the selecting of the research subject 602, data representative of a study participation assignment to a subject device used by the research subject (not explicitly shown, but which may include any suitable mobile device, personal computer, or other such computing device).

As another example, prospective designations 702 illustrated by solid and dotted arrows from system 100 to select research subjects 602 (i.e., research subjects 602-1, 602-2, 602-3, 602-5, and 602-6 in this example) illustrate another way that system 100 may perform selection process 700. In this example, it is not assumed that each research subject 602 in subject pool 600 is necessarily committed to participating in research studies for which they are designated. Rather, research subjects 602 in this type of example may be given an opportunity to accept offers for which they have been determined to be viable candidates. In contrast to the employee/manager analogy mentioned above, this approach may be more analogous, for instance, to the way a ride share employee or contractor may accept potential ride assignments when logged onto a ride orchestration system.

For this type of approach, it will be understood that study participation offers may be made to a larger number of research subjects 602 than will ultimately accept the offer and join research subject group 316. Specifically, as shown, while prospective designations 702 are made for research subjects 602-1, 602-2, 602-3, 602-5, and 602-6, final designations 704 are made only for a subset of these research subjects who accept the offer (i.e., research subjects 602-1, 602-3, and 602-6). In other words, it will be understood that the research subjects associated with dotted arrows for prospective designations 702 (i.e., research subjects 602-2 and 602-5) may have received but declined an offer to participate in the research study. More particularly, in this type of implementation, the designating of research subjects 314 for inclusion in research subject group 316 may include: 1) determining that a research subject 602 satisfies a certain set of criteria (e.g., defined by research subject criteria 406); 2) transmitting, based on the determining that the research subject 602 satisfies the set of criteria, data representative of a study participation offer to a subject device (not explicitly shown in FIG. 7) used by the research subject 602; 3) receiving, subsequent to the transmitting of the data representative of the study participation offer, data representative of a study participation acceptance from the subject device; and 4) selecting, in response to the receiving of the data representative of the study participation offer, the research subject 602 for inclusion in research subject group 316.

As illustrated by both example approaches above, it may often be the case that certain research subjects 602 included in subject pool 600 do not satisfy the set of criteria to a suitable extent and thus, at least for a first round of study participation offers, are not prospectively designated for inclusion in research subject group 316. For example, research subjects 602-4 and 602-N are shown in FIG. 7 to be examples of non-designated potential research subjects. In certain cases, some of these non-designated research subjects may meet some of research subject criteria 406 but may not be as ideal of candidates for the research opportunity as others in the pool. As such, these research subjects 602 may be non-designated for a first round of study participation assignments or offers, but may be considered for subsequent rounds of study participation assignments or offers if it turns out that more ideal candidates are unavailable (e.g., drop out or fail to volunteer) and more research subjects 314 are needed to satisfy study objectives.

Returning to FIG. 3, once system 100 has designated each of research subjects 314 to form research subject group 316, the research study may commence in accordance with parameters that have been provided (e.g., parameters 404 of input dataset 402 described above, etc.). In examples described herein, research studies being requested by client devices 302 and initiated, conducted, and/or otherwise enabled or facilitated by system 100 have generally been described as brain studies (and computer-enabled brain research studies in particular). As has been mentioned and as will be described in more detail below, brain studies may involve monitoring or testing the brain functions of research subjects using brain interface systems 318 and/or other suitable brain interface systems described herein or as may serve a particular implementation. While brain studies are described as a primary example, however, it will be understood that various principles described herein may find application in other types of research studies (e.g., other computer-enabled research studies) that are not specifically related to the brain. For example, heart studies that utilize equipment such as a pulse detection device or other heart interface system may be initiated and conducted by a research support computing system such as system 100 in an analogous way as is described herein for brain studies.

As has been mentioned, different site configurations may be employed by different implementations of system 100. For example, different site configurations may be tailored to different types of research subject groups (e.g., research subject groups with research subjects whose only brain interface system access is at a research clinic setting, research subject groups with research subjects that have access to their own brain interface systems, etc.) and/or to different types research studies (e.g., research studies that measure brain activity when subjects are performing tasks that can be performed in a clinical setting, research studies that measure brain activity when subjects are performing tasks that require more mobility or different environmental factors than can be provided in the clinical setting, etc.).

Figure 8A:
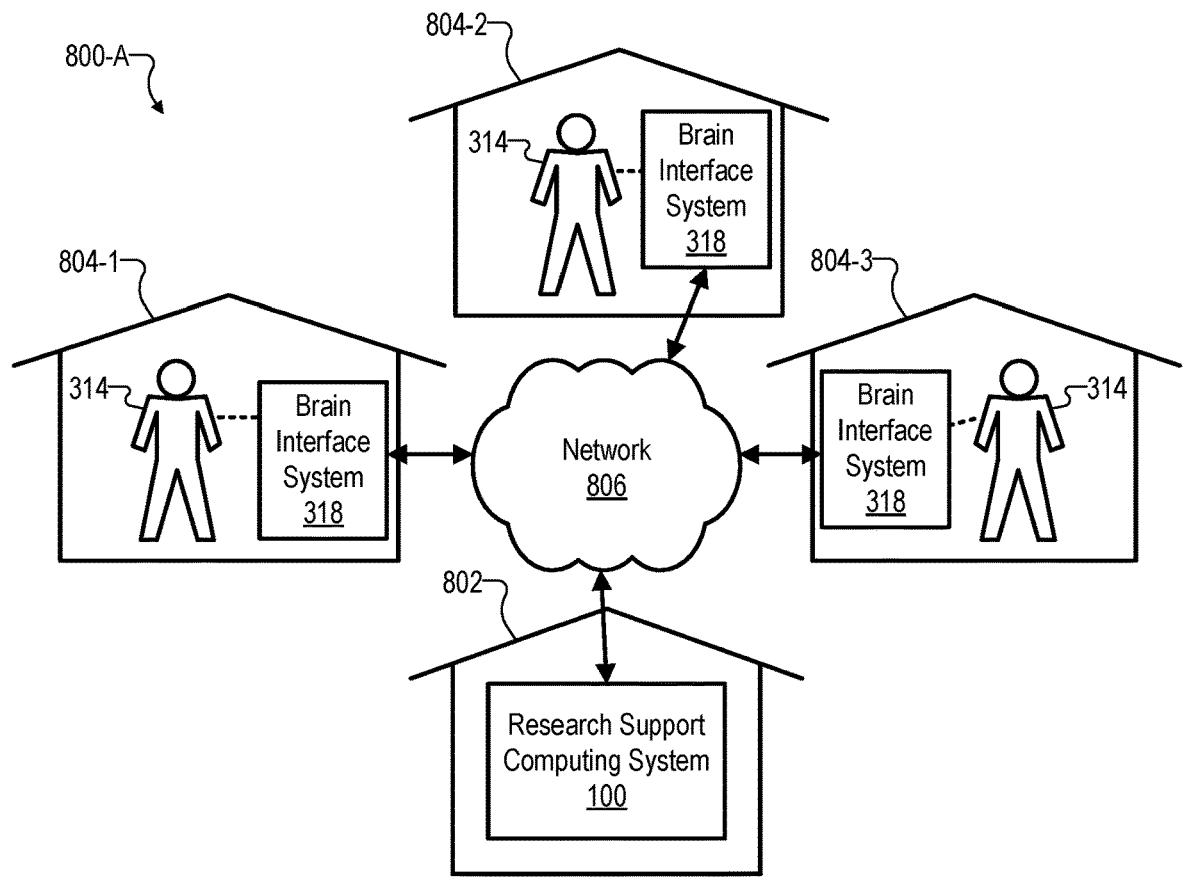
FIGS. 8A and 8B show different illustrative site configurations that may be employed as a research support computing system and a plurality of brain interface systems are used to conduct a computer-enabled brain research study according to principles described herein.
Figure 8B:
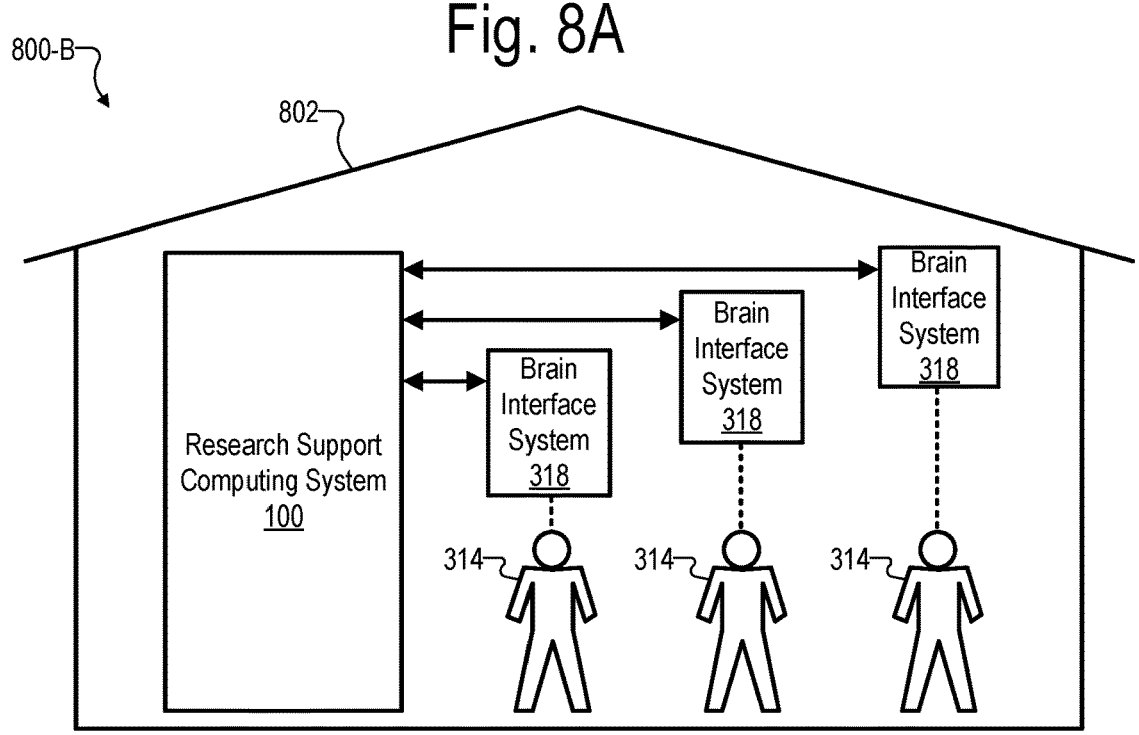

To illustrate, FIGS. 8A and 8B show different illustrative site configurations 800 (i.e., site configuration 800-A depicted in FIG. 8A and site configuration 800-B depicted in FIG. 8B) that may be employed as system 100 and brain interface systems 318 interoperate to conduct a computer-enabled brain research study in accordance with principles described herein.

Specifically, site configuration 800-A of FIG. 8A shows a scenario in which a site 802 of system 100 (e.g., a clinical site, a data center housing one or more server computer or other compute nodes, etc.) is separate and remote from respective sites 804 (e.g., sites 804-1 through 804-3 illustrated in this example) at which different research subjects 314 and their respective brain interface systems 318 are located. As such, each brain interface system 318 used by each research subject 314 in this example may be implemented as a brain data acquisition system used by the research subject at a different site 804 that is remote from site 802 of system 100. In certain examples, site 802 may be a central site located at a particular location while sites 804 may be distributed over a wider geographic area (e.g., throughout a city, state, country, etc.). Sites 804 may represent any suitable place of residence, place of work, school facility, vehicle, outdoor area, or other location at which a particular research subject 314 may engage in a brain monitoring session using a brain interface system 318. As shown, a network 806 (e.g., the Internet or any other suitable network described herein) may be used to communicatively couple the different brain interface systems 318 to system 100.

In contrast, site configuration 800-B of FIG. 8B shows a different scenario in which site 802 of system 100 is the same site at which research subjects 314 and associated brain interface systems 318 for each research subject are located. As such, each brain interface system 318 used by each research subject 314 in this example may be implemented as a brain data acquisition system used by the research subject at the same site 802 of system 100. For instance, site 802 may be a research clinic or other setting at which brain interface systems 318 are kept and research subjects may come in to engage in research-related activities. In certain examples, a network analogous to network 806 (e.g., a local area network, etc.) may be utilized in this type of scenario, though this is not explicitly shown in FIG. 8B. In other examples, due to the close proximity of system 100 and the brain interface systems 318 at the same site, it may be possible for brain interface systems 318 to interconnect with system 100 by way of a direct connection instead of network-based link.

As has been mentioned above, certain accessibility features of brain interface systems 318 used by research subjects 314 may enable various advantages that have been described herein. For example, one accessibility feature of a brain interface system 318 employed in configuration 300 with system 100 is a relatively low price point for the brain interface system that allows it to be owned by, leased by, shipped to, or otherwise reasonably accessed by a research subject from a site that is remote to system 100 (e.g., one of sites 804). Another accessibility feature example may be the relatively portable size of a brain interface system that allows for a wide array of tasks to be performed while a research subject is being monitored. For instance, certain brain interface systems 318 may be worn like a hat or under a hood or the like and worn while everyday activities such as walking, driving, shopping, working, and so forth are performed in everyday life work environments. Still other accessibility features of brain interface systems 318 may involve a discrete design (e.g., so that research subjects do not feel self-conscious while wearing the devices), a non-invasive nature of the brain interface systems, an ease of use of the brain interface systems (e.g., so that research subjects can be easily trained on how to properly use the devices, etc.), safety features that allow non-specialized personnel to operate the systems, and so forth. Two different types of brain interface systems 318 that comport these and/or other accessibility features will now be described in relation to FIGS. 9 and 10.

Figure 9:
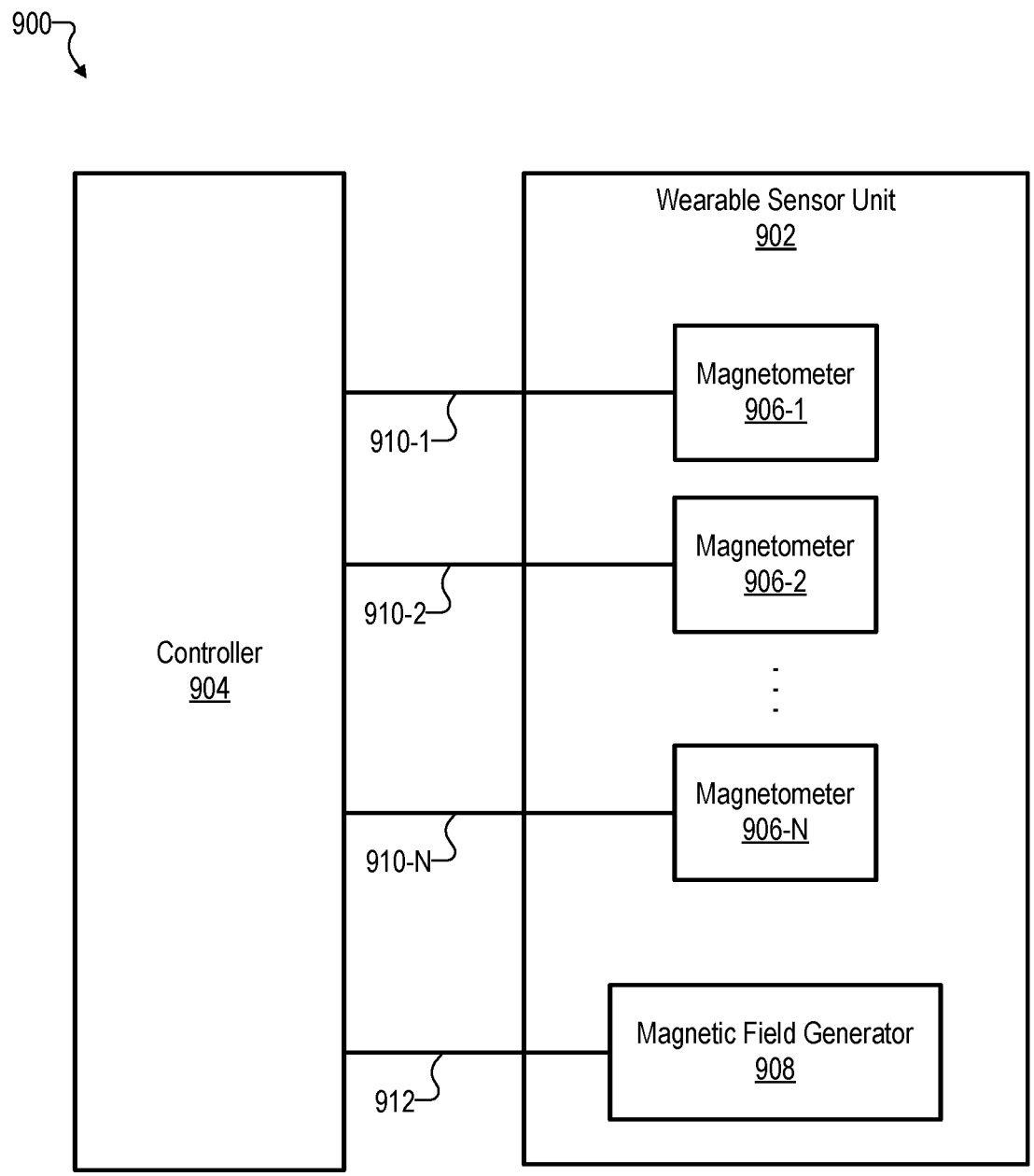
FIG. 9 shows an illustrative brain interface system including a magnetic field measurement system according to principles described herein.

FIG. 9 shows an illustrative brain interface system 318 that may be used by research subject 314 and that includes or is implemented by a magnetic field measurement system 900. More particularly, magnetic field measurement system 900 may include or implement a magnetoencephalographic ("MEG")-based brain data acquisition system in accordance with principles that will now be described. Data generated by magnetic field measurement system 900 or another portable or stationary data acquisition system may be securely stored in in a database this is integrated with the non-invasive brain interface system or implemented as an external component.

Magnetic field measurement system 900 is described more fully in U.S. patent application Ser. No. 16/862,879, filed Apr. 30, 2020; and U.S. Provisional Application No. 63/058,616, filed Jul. 30, 2020, which applications are incorporated by reference herein in their entirety. Magnetic field measurement system 900 can be used in a magnetically shielded environment which can allow for user movement as described for example in U.S. Provisional Application No. 63/076,015, filed Sep. 9, 2020, which is incorporated herein by reference in its entirety. Systems and methods for pose (e.g., position or orientation or both) and motion tracking used to track a position or orientation of a research subject and the subject's brain interface system while the research subject is in a magnetically shielded environment are described more fully in U.S. Provisional Application No. 63/076,880, filed Sep. 10, 2020, and incorporated herein by reference in its entirety. Systems and methods in which optical data is used to register, validate, and enhance magnetoencephalography (MEG) data, acquired from a subject using wearable MEG instrumentation are described more fully in U.S. Provisional Application No. 63/080,248, filed Sep. 18, 2020, and incorporated herein by reference in its entirety.

As shown, magnetic field measurement system 900 includes a wearable sensor unit 902 and a controller 904. Wearable sensor unit 902 includes a plurality of magnetometers 906-1 through 906-N, optically pumped magnetometers, (collectively "magnetometers 906") and a magnetic field generator 908. Wearable sensor unit 902 may include additional components (e.g., one or more magnetic field sensors, position sensors, optical sensors, orientation sensors, accelerometers, image recorders, detectors, etc.) as may serve a particular implementation. Magnetic field measurement system 900 may be used in MEG applications and/or any other applications that measures relatively weak magnetic fields.

Wearable sensor unit 902 may be configured to be worn by a research subject (e.g., on a head of the subject). In some examples, wearable sensor unit 902 may be portable. In other words, wearable sensor unit 902 may be small and light enough to be easily carried by a subject and/or worn by the subject while moving around and/or otherwise performing daily activities.

Any suitable number of magnetometers 906 may be included in wearable sensor unit 902. For example, wearable sensor unit 902 may include an array of nine, sixteen, twenty-five, or any other suitable number of magnetometers 906 as may serve a particular implementation.

Magnetometers 906 may each be implemented by any suitable combination of components configured to be sensitive enough to detect a relatively weak magnetic field (e.g., magnetic fields that come from the brain). For example, each magnetometer may include a light source, a vapor cell such as an alkali metal vapor cell (the terms "cell", "gas cell", "vapor cell", and "vapor gas cell" are used interchangeably herein), a heater for the vapor cell, and a photodetector (e.g., a signal photodiode). Examples of suitable light sources may include, but are not limited to, a diode laser (such as a vertical-cavity surface-emitting laser ("VCSEL"), a distributed Bragg reflector laser ("DBR"), a distributed feedback laser ("DFB"), a light-emitting diode ("LED"), a lamp, or any other suitable light source. In some embodiments, the light source may include two light sources: a pump light source and a probe light source. These magnetometer components, and manners in which they operate to detect magnetic fields, are described in more detail in U.S. patent application Ser. No. 16/457,655, filed Jun. 28, 2019; U.S. patent application Ser. No. 16/213,980, filed Dec. 7, 2018 28 (now U.S. patent Ser. No. 10/627,460); U.S. patent application Ser. No. 16/752,393, filed Jan. 24, 2020; U.S. patent application Ser. No. 16/820,131 filed Mar. 16, 2020; U.S. patent application Ser. No. 16/850,444; and U.S. patent application Ser. No. 16/984,752, filed Aug. 4, 2020, which applications are incorporated by reference herein in their entirety.

Magnetic field generator 908 may be implemented by one or more components configured to generate one or more compensation magnetic fields that actively shield magnetometers 906 (including respective vapor cells) from ambient background magnetic fields (e.g., the Earth's magnetic field, magnetic fields generated by nearby magnetic objects such as passing vehicles, electrical devices and/or other field generators within an environment of magnetometers 906, and/or magnetic fields generated by other external sources). For example, magnetic field generator 908 may be configured to generate compensation magnetic fields in the Z direction, X direction, and/or Y direction (all directions are with respect to one or more planes within which the magnetic field generator 908 is located). The compensation magnetic fields are configured to cancel out, or substantially reduce, ambient background magnetic fields in a magnetic field sensing region with minimal spatial variability.

Controller 904 is configured to interface with (e.g., control an operation of, receive signals from, etc.) magnetometers 906 and the magnetic field generator 908. Controller 904 may also interface with other components that may be included in wearable sensor unit 902. In some examples, controller 904 may be referred to as a "single" controller 904. This means that only one controller is used to interface with all of the components of wearable sensor unit 902. For example, controller 904 may be the only controller that interfaces with magnetometers 906 and magnetic field generator 908. This is in contrast to conventional configurations in which discrete magnetometers each have their own discrete controller associated therewith. It will be recognized, however, that any number of controllers may interface with components of magnetic field measurement system 900 as may suit a particular implementation.

As shown, controller 904 may be communicatively coupled to each of magnetometers 906 and magnetic field generator 908. For example, FIG. 9 shows that controller 904 is communicatively coupled to magnetometer 906-1 by way of communication link 910-1, to magnetometer 906-2 by way of communication link 910-2, to magnetometer 906-N by way of communication link 910-N, and to magnetic field generator 908 by way of communication link 912. In this configuration, controller 904 may interface with magnetometers 906 by way of communication links 910-1 through 910-N (collectively "communication links 910") and with magnetic field generator 908 by way of communication link 912.

Communication links 910 and communication link 912 may be implemented by any suitable wired connection as may serve a particular implementation. For example, communication links 910 may be implemented by one or more twisted pair cables while communication link 912 may be implemented by one or more coaxial cables. Alternatively, communication links 110 and communication link 112 may both be implemented by one or more twisted pair cables.

Controller 904 may be implemented in any suitable manner. For example, controller 904 may be implemented by an FPGA, an ASIC, a digital signal processor ("DSP"), a microcontroller, and/or any other suitable processing and/or control circuitry as may serve a particular implementation.

In some examples, controller 904 may be implemented on one or more printed circuit boards ("PCBs") included in a single housing. In cases where controller 904 is implemented on a PCB, the PCB may include various connection interfaces configured to facilitate communication links 910 and 912. For example, the PCB may include one or more twisted pair cable connection interfaces to which one or more twisted pair cables may be connected (e.g., plugged into) and/or one or more coaxial cable connection interfaces to which one or more coaxial cables may be connected (e.g., plugged into). In some examples, controller 904 may be implemented by or within a computing device such as described herein or as may serve a particular implementation.

An alternative magnetic field measurement system may include or implement magnetocardiography (MCG) technologies to measure cardiac activity by recording magnetic fields produced by electrical currents occurring naturally in the heart. Such magnetic field measurement system is described more fully in U.S. Provisional Patent Application Ser. No. 63/136,093, filed Jan. 11, 2021.

Figure 10:
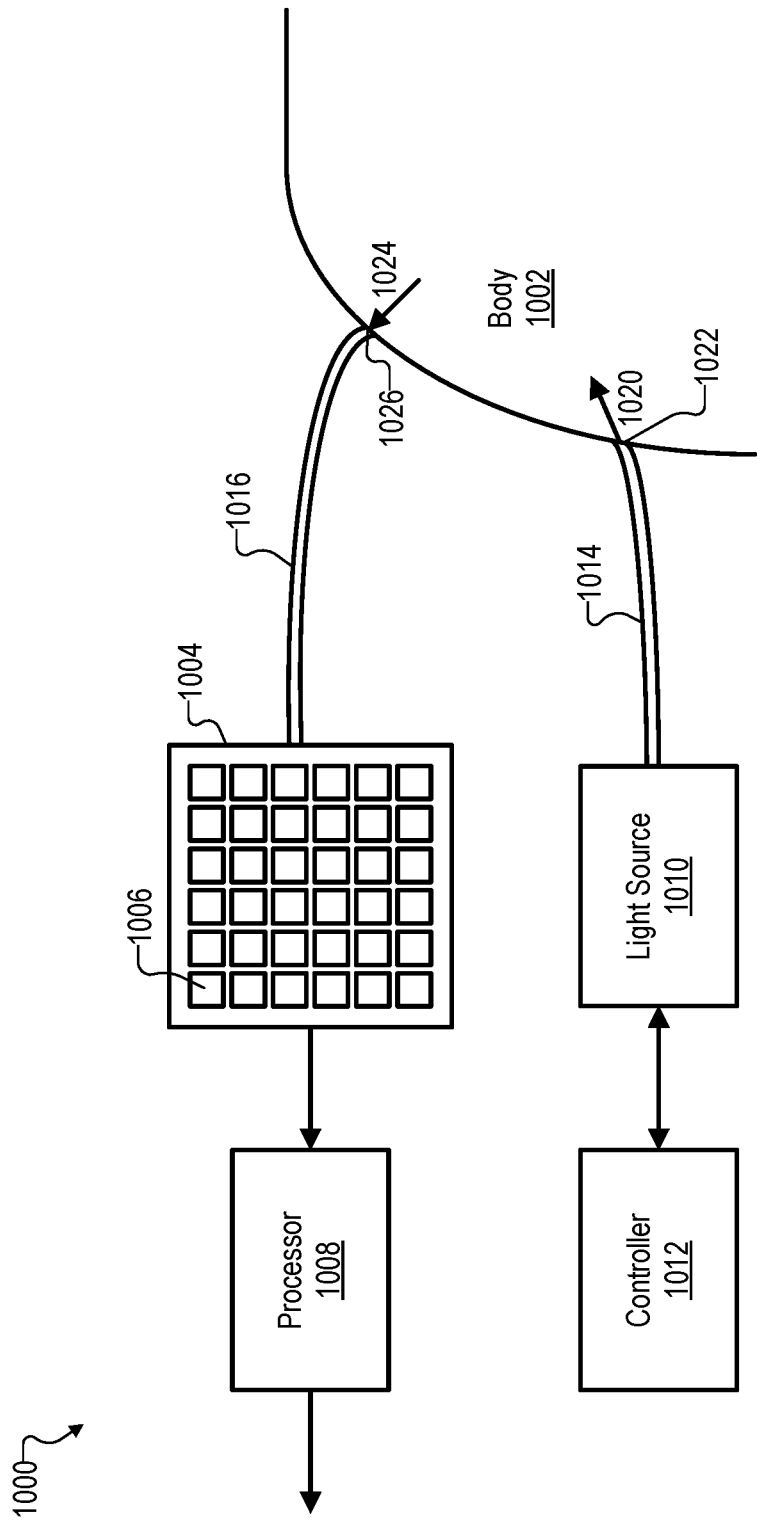
FIG. 10 shows an illustrative brain interface system including an optical measurement system according to principles described herein.

FIG. 10 shows another illustrative brain interface system 318 that may be used by research subject 314 and that, in this example, includes or is implemented by an optical measurement system 1000. More particularly, optical measurement system 1000 may include or implement an optical-based brain data acquisition system in accordance with principles that will now be described. As with magnetic field measurement system 900, data generated by optical measurement system 1000 may be securely stored in a database that is integrated with the non-invasive brain interface system or implemented as an external component.

Optical measurement system 1000 may be implemented by any of the optical measurement systems described in U.S. Provisional Patent Application No. 63/120,650, filed Dec. 2, 2020; U.S. Provisional Patent Application No. 63/079,194, filed Sep. 16, 2020; U.S. Provisional Patent Application No. 63/081,754, filed Sep. 22, 2020, U.S. Provisional Patent Application No. 63/038,459, filed Jun. 12, 2020, U.S. Provisional Patent Application No. 63/038,468, filed Jun. 12, 2020, U.S. Provisional Patent Application No. 63/038,481, filed Jun. 12, 2020, U.S. Provisional Patent Application No. 63/064,688, filed Aug. 12, 2020, and U.S. Provisional Patent Application No. 63/086,350, filed Oct. 1, 2020, which applications are incorporated herein by reference in their entireties.

Optical measurement system 1000 in FIG. 10 may be configured to perform an optical measurement operation with respect to a body 1002. In certain examples, optical measurement system 1000 may be portable and/or wearable by a research subject (e.g., one of research subjects 314).

In some implementations, optical measurement operations performed by optical measurement system 1000 may be associated with a time domain-based optical measurement technique. Example time domain-based optical measurement techniques may include, but are not limited to, time-correlated single-photon counting ("TCSPC"), time domain near infrared spectroscopy ("TD-NIRS"), time domain diffusive correlation spectroscopy ("TD-DCS"), time domain digital optical tomography ("TD-DOT"), and so forth.

As shown, optical measurement system 1000 may include a detector 1004 that includes a plurality of individual photodetectors (e.g., photodetectors 1006), a processor 1008 coupled to detector 1004, a light source 1010, a controller 1012, and optical conduits 1014 and 1016 that may serve as light guides. In certain embodiments, one or more of these components may not be considered to be included within or to be a part of optical measurement system 1000. For example, in implementations where optical measurement system 1000 is wearable by a research subject 314, processor 1008 and/or controller 1012 may be separate from optical measurement system 1000 and not configured to be worn by the research subject 314.

Detector 1004 may include any number of photodetectors 1006 as may serve a particular implementation, such as $2^n$ photodetectors (e.g., 256 photodetectors, 512 photodetectors, . . . , 16384 photodetectors, etc.), where n is an integer greater than or equal to one (e.g., 4, 5, 8, 10, 11, 14, etc.). Photodetectors 1006 may be arranged in any suitable manner.

Photodetectors 1006 may each be implemented by any suitable circuit configured to detect individual photons of light incident upon photodetectors 1006. For example, each photodetector 1006 may be implemented by a single photon avalanche diode ("SPAD") circuit and/or other circuitry as may serve a particular implementation.

Processor 1008 may be implemented by one or more physical processing (e.g., computing) devices. In some examples, processor 1008 may execute instructions (e.g., software) configured to perform one or more of the operations described herein.

Light source 1010 may be implemented by any suitable component configured to generate and emit light. For example, light source 1010 may be implemented by one or more laser diodes, DFB lasers, super luminescent diodes ("SLDs"), LEDs, diode-pumped solid-state ("DPSS") lasers, super luminescent light emitting diode ("sLEDs"), VCSELs, titanium sapphire lasers, a micro light emitting diodes ("mLEDs"), and/or any other suitable laser or light source configured to emit light in one or more discrete wavelengths or narrow wavelength bands. In some examples, the light emitted by light source 1010 may be high coherence light (e.g., light that has a coherence length of at least 5 centimeters) at a predetermined center wavelength. In some examples, the light emitted by light source 1010 may be emitted as a plurality of alternating light pulses of different wavelengths.

Light source 1010 is controlled by controller 1012, which may be implemented by any suitable computing device (e.g., processor 1008), integrated circuit, and/or combination of hardware and/or software as may serve a particular implementation. In some examples, controller 1012 is configured to control light source 1010 by turning light source 1010 on and off and/or setting an intensity of light generated by light source 1010. Controller 1012 may be manually operated by a user, or may be programmed to control light source 1010 automatically.

Light emitted by light source 1010 travels via an optical conduit 1014 (e.g., a light pipe, a light guide, a waveguide, a single-mode optical fiber, and/or or a multi-mode optical fiber) to body 1002 (e.g., a body of a particular research subject 314 who is using optical measurement system 1000). Body 1002 may include any suitable turbid medium. For example, in some implementations, body 1002 may be the head or another body part of research subject 314 (e.g., or of another human subject, animal subject, or non-living object). For illustrative purposes, it will be assumed in the examples provided herein that body 1002 is a human head.

As indicated by arrow 1020, light emitted by light source 1010 may enter body 1002 at a first location 1022 on body 1002. Accordingly, a distal end of optical conduit 1014 may be positioned at (e.g., right above, in physical contact with, or physically attached to) first location 1022 (e.g., to a scalp of the subject). In some examples, the light may emerge from optical conduit 1014 and spread out to a certain spot size on body 1002 to fall under a predetermined safety limit. At least a portion of the light indicated by arrow 1020 may be scattered within body 1002.

As used herein, "distal" means nearer, along the optical path of the light emitted by light source 1010 or the light received by detector 1004, to the target (e.g., within body 1002) than to light source 1010 or detector 1004. Thus, the distal end of optical conduit 1014 is nearer to body 1002 than to light source 1010, and the distal end of optical conduit 1016 is nearer to body 1002 than to detector 1004. Additionally, as used herein, "proximal" means nearer, along the optical path of the light emitted by light source 1010 or the light received by detector 1004, to light source 1010 or detector 1004 than to body 1002. Thus, the proximal end of optical conduit 1014 is nearer to light source 1010 than to body 1002, and the proximal end of optical conduit 1016 is nearer to detector 1004 than to body 1002.

As shown, the distal end of optical conduit 1016 (e.g., a light pipe, a light guide, a waveguide, a single-mode optical fiber, and/or a multi-mode optical fiber) may be positioned at (e.g., right above, in physical contact with, or physically attached to) output location 1026 on body 1002. In this manner, optical conduit 1016 may collect at least a portion of the scattered light (indicated as light 1024) as it exits body 1002 at location 1026 and carry light 1024 to detector 1004. Light 1024 may pass through one or more lenses and/or other optical elements (not shown) that direct light 1024 onto each of the photodetectors 1006 included in detector 1004.

Photodetectors 1006 may be connected in parallel in detector 1004. An output of each of photodetectors 1006 may be accumulated to generate an accumulated output of detector 1004. Processor 1008 may receive the accumulated output and determine, based on the accumulated output, a temporal distribution of photons detected by photodetectors 1006. Processor 1008 may then generate, based on the temporal distribution, a histogram representing a light pulse response of a target (e.g., tissue, blood flow, etc.) in body 1002.

Returning to FIG. 3, system 100 may interoperate with brain interface systems 318 (e.g., implementations of magnetic field measurement system 900, optical measurement system 1000, or other suitable brain data acquisition systems) to collect raw research data for each research subject 314 (e.g., brain data collected for each research subject 314 during testing circumstances dictated by study parameters provided by user 304). As mentioned above in relation to FIG. 4, output dataset 408 may then be provided by system 100 to a client device 302 with raw research data 410, processed research results data 412, and/or any other suitable data.

Raw research data 410 may include data that is detected for a particular research subject 314 and is in an unprocessed form configured to allow for the research data to be processed by a client device 302 to which output dataset 408 is transmitted and/or by some other computing system that receives the research data from that client device 302. In these examples, the user 304 may only use system 100 to help initiate and conduct the computer-enabled research study, but may prefer to analyze, process, and make research conclusions regarding the data without use of system 100. Accordingly, raw research data 410 provided back to the client device 302 may enable user 304 full control over the processing of the raw data on his or her end.

In the same or other examples, it may be desired by certain users 304 to leverage the processing resources of system 100 to not only collect the raw data, but also to at least partially analyze, derive conclusions or research results, or otherwise process the captured research data in any suitable way. For example, system 100 may process (subsequent to receiving raw research data 410 from brain interface systems 318) the research data detected for the research subject 314 to produce research results data 412 that is derived from and different than the raw research data. As such, output dataset 408 provided to the client device 302 may include the results data 412 that is derived from and different from raw research data 410, as shown in FIG. 4.

The processing on raw research data received from brain interface systems 318 may involve any suitable types of processing, preprocessing, analysis, or the like as may serve a particular implementation. In certain examples, system 100 may perform preprocessing of research data by sending incoming data through an automated data quality check that flags datasets as a whole and then portions out or extracts the datasets across time that are corrupt. Conditioning flagged data may entail using a wavelet method that corrects corrupt time windows of data or datasets. In certain examples, data may be detrended (e.g., through poly fitting, wavelet or high pass operations, etc.), regressed (e.g., including a time-shifted principal component regression in real-time), decimated, or otherwise preprocessed in preparation for additional processing. For instance, preprocessed data may be analyzed at the sensor level to be epoched, time aligned to behavior, converted into time-frequency, averaged, clustered, correlated, classified into states, manifold-regressed to find a common sub-space, or otherwise processed or analyzed on an inter-individual or group basis.

In the same or other examples, the processing of the research data performed by system 100 may include a source reconstruction analysis that estimates, based on the research data detected for the research subject, one or more sources (within a brain of the research subject 314) that generated one or more signals represented by the research data detected for the research subject 314. For instance, preprocessed data may be utilized for source reconstruction by estimating the sources in the brain that generated the signal seen on the sensor and by allowing a user to define what brain regions were specifically active and how they are connected.

Once such source reconstruction has been performed, the processing of the research data by system 100 may involve a connectivity analysis in which system 100 defines a spatiotemporal activation pattern across a plurality of regions of a brain of the research subject 314 to indicate a relationship between neural oscillations and functional connectivity of the brain. In this way, a source reconstructed signal may be utilized to define the spatiotemporal activation patterns and how they co-vary across different regions of the brain. These functional connectivity assessments may occur in the time domain as well as the frequency domain using linear (e.g., correlation) and nonlinear (e.g., mutual information) methods. This analysis may demonstrate the relationship between neural oscillations and functional connectivity of the brain, and may help build intuition on the path of information flow within the brain during the activity of the experiment.

In certain processing or analysis examples such as those described above or other examples, system 100 may perform analysis beginning at the sensor level and looking first at individual sensor parameters. Single channel analysis parameters may include, for example, spectral analysis, signal complexity, signal regularity, and signal predictability. Spectral analysis will look for the increasing and decreasing measures of many parameters (e.g., absolute power, entropy, etc.) for all the frequency bands. Epochs of neural signal for each channel may then be transformed into the time-frequency domain, and the resulting spectral power estimations per sensor may be averaged over epochs to generate time-frequency plots of mean spectral density to start looking at whole head sensor analysis. Such sensor-level data may be normalized by dividing the power value of each time-frequency bin by the respective bin's baseline power. Sensor-level spectrograms may then be used for beamforming analyses. Spatial filters may be employed in the frequency domain to calculate source power for the entire brain volume, using paired-sample t-tests for each of the time-frequency bins of interest. Tests may then be conducted across different task conditions to identify areas generating oscillatory brain responses observed in sensor space. Following sensor-level analysis, a source reconstruction method may be applied to create source space.

Any of various techniques may be employed to perform network analysis in source space to report on activation in regions of interest as well as connectivity across the brain during different task conditions. For instance, these techniques may include minimum norm estimation to detect synchronous and distributed neural activity of different cortical areas, coherence to detect the degree of similarity of frequency components of two time series (of simultaneous values or leading and lagging relationships), evaluating synchronization likelihood (based on state space embedding) to detect the strength of synchronization of two time series, nonlinear forecasting and cross mutual information functions to measure for the predictability of one time series when a second series is known, phase lag index to evaluate the distribution of phase differences across observations, and/or any other techniques as may serve a particular implementation.

In the description above, examples have shown how client devices 302 may transmit an input dataset 402 that defines parameters and criteria of a desired research study to be performed, how system 100 may form research subject group 316 and interoperate with brain interface systems 318 to capture and process research and results data for the research study, and how such data may then eventually be provided back to the requesting client device 302 in an output dataset 408. While not yet described in detail, however, it will be understood that certain regulatory constraints (e.g., laws and/or regulations imposed by governments, ethics organizations, etc.) may need to be accounted for in the planning of a research study before the study can proceed with testing research subjects 314 of research subject group 316. For conventional research studies, acquiring regulatory approval for a prospective research study may involve registration and requestion processes, filling out and submitting application forms to a regulatory authority, and waiting to receive approval or denial of the research application. Advantageously, system 100 may, for certain computer-enabled brain research studies, significantly simplify and facilitate this approval process to allow certain research studies to be approved immediately and without any additional effort by users 304, or to at least reduce the effort that is required of a user 304 in cases where the user still must traverse the approval process to some degree.

As shown in FIG. 3, the automatic facilitation of a regulatory approval process may involve communications between system 100 and regulatory approval authority system 320. Regulatory approval authority system 320 may represent any computing system or set of computing systems operated by a regulatory approval authority (e.g., an institutional review board ("IRB"), an independent ethics committee ("IEC"), an ethical review board ("ERB"), a research ethics board ("REB"), a governmental agency or committee, etc.) that is used to receive, process, and ultimately approve or reject applications for human research studies.

Figure 11:
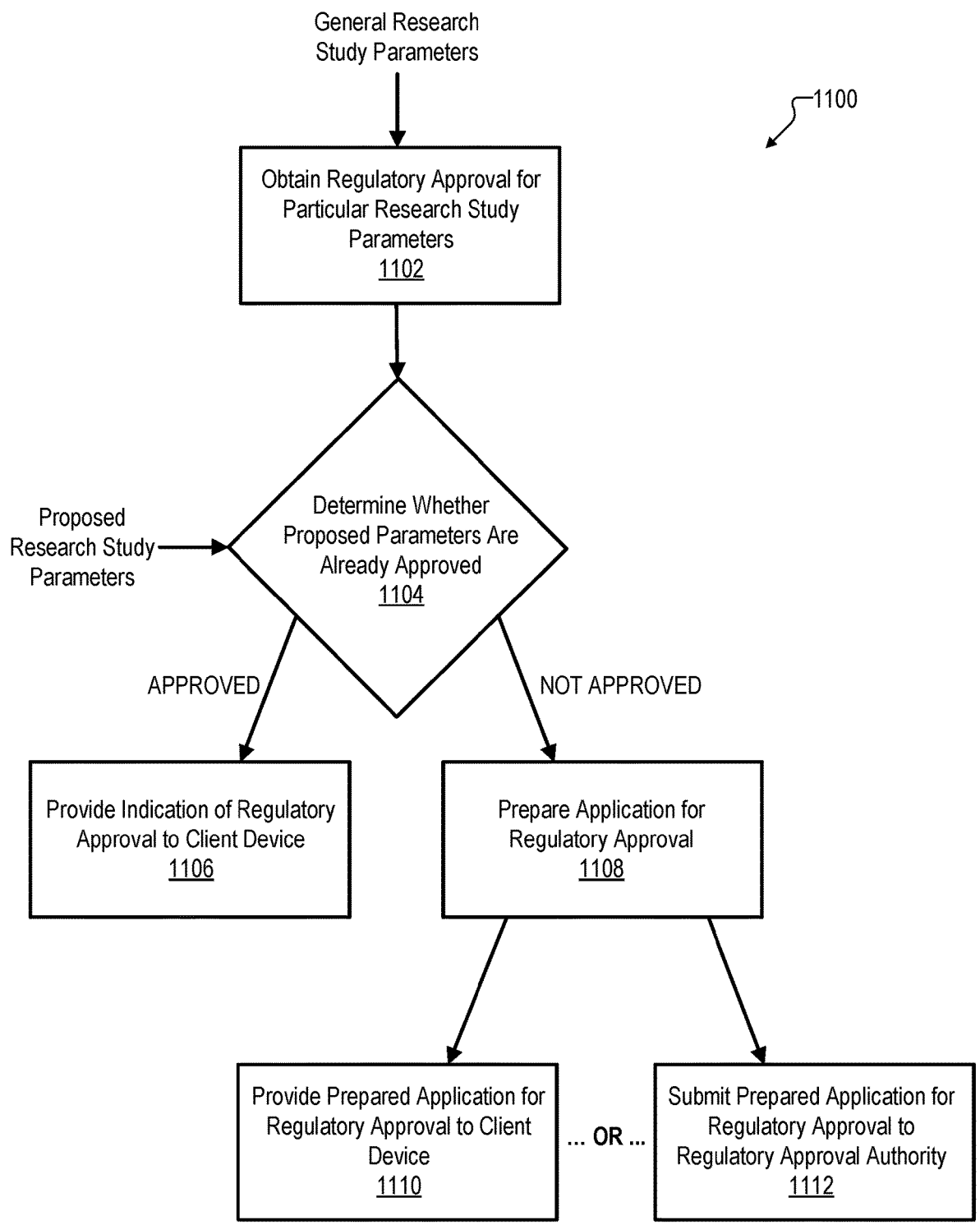
FIG. 11 shows an illustrative flow diagram depicting different ways a research support computing system may automatically facilitate a regulatory approval process according to principles described herein.

Communicating with regulatory approval authority system 320 and/or other components of configuration 300 (e.g., client devices 302, etc.), system 100 may automatically facilitate (e.g., based on a set of parameters 404 received in an input dataset 402 from a client device 302) a regulatory approval process associated with the research study being described by the input dataset. To illustrate, FIG. 11 shows a flow diagram 1100 depicting certain of the various ways that system 100 may automatically facilitate the regulatory approval process. Operations performed at each of various steps 1102-1112, as well as data and previous decisions that may be accounted for at those steps, will now be described in relation to FIG. 11.

At step 1102, system 100 may obtain regulatory approval for particular research study parameters based on a set of general research study parameters (e.g., generic research study parameters not necessarily associated with any particular research study, but that are anticipated to apply for various potential research studies). For instance, based on the types of behavioral characteristics, demographic attributes, and other data that system 100 may acquire for a prospective research study by way of computer interface 310 (e.g., particular parameters or combinations of parameters that are available for selection from drop down menus of graphical user interface 500, etc.) preapproval for various types of research studies may be obtained. In this way, research studies that are later proposed may be immediately approved if they have already been fully considered and preapproved by the regulatory authority.

For example, at step 1104, system 100 may receive proposed research study parameters (e.g., a set of parameters 404 of an input dataset 402) that happen to overlap or align with the general research study parameters for which preapproval was obtained at step 1102. Accordingly, system 100 may determine at step 1104 that the proposed parameters are already approved and flow may follow the "APPROVED" arrow from step 1104 to step 1106, where system 100 may provide an indication of immediate, real-time regulatory approval to the client device 302. In other words, in this example, system 100 may automatically facilitate the regulatory approval process by: 1) determining (at step 1104) that preapproval for research studies characterized by the set of parameters defining the research study has already been obtained; and 2) providing (at step 1106) an indication of regulatory approval for the research study to client device 302 based on the determining that the preapproval has already been obtained.

In other examples, system 100 may determine at step 1104 that at least some of the proposed criteria or parameters have not already been approved and flow may follow the "NOT APPROVED" arrow from step 1104 to step 1108. At step 1108, system 100 may prepare an application (e.g., collect data, fill out forms, etc.) that must be submitted to request regulatory approval for the prospective research study whose parameters are not already preapproved.

In certain implementations, this prepared application may be automatically submitted to regulatory approval authority system 320 to initiate the approval process and thereby save user 304 much of the work in collecting data, putting together the application, and submitting the request for consideration. In such examples, the automatic facilitating of the regulatory approval process by system 100 may thus be said to include: 1) determining (at step 1104) that preapproval for research studies characterized by the set of parameters defining the research study has not yet been obtained; 2) preparing (at step 1108) an application configured to be submitted as part of the regulatory approval process based on the set of parameters defining the research study and based on the determining that the preapproval has not yet been obtained; and 3) submitting (at step 1110) data representative of the prepared application to a computing system associated with a regulatory approval authority (e.g., regulatory approval authority system 320).

In other implementations, it may not be possible or desirable for the prepared application to be automatically submitted to regulatory approval authority system 320. For instance, there may be certain aspects of the application that system 100 cannot fully complete and that require the attention of user 304 before submission. In such examples, the prepared application may be provided to client device 302 to allow user 304 to complete the application if necessary and to manually oversee submission of the application. In this scenario, the automatic facilitating of the regulatory approval process by system 100 may thus include: 1) determining (at step 1104) that preapproval for research studies characterized by the set of parameters defining the research study has not yet been obtained; 2) preparing (at step 1108) an application configured to be submitted as part of the regulatory approval process based on the set of parameters defining the research study and based on the determining that the preapproval has not yet been obtained; and 3) providing (at step 1112) data representative of the prepared application configured to be submitted as part of the regulatory approval process to client device 302.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory (DRAM), which typically constitutes a main memory. Common forms of computer-readable media include, for example, a disk, hard disk, magnetic tape, any other magnetic medium, a compact disc read-only memory (CD-ROM), a digital video disc (DVD), any other optical medium, random access memory (RAM), programmable read-only memory (PROM), electrically erasable programmable read-only memory (EPROM), FLASH-EEPROM, any other memory chip or cartridge, or any other tangible medium from which a computer can read.

Figure 12:
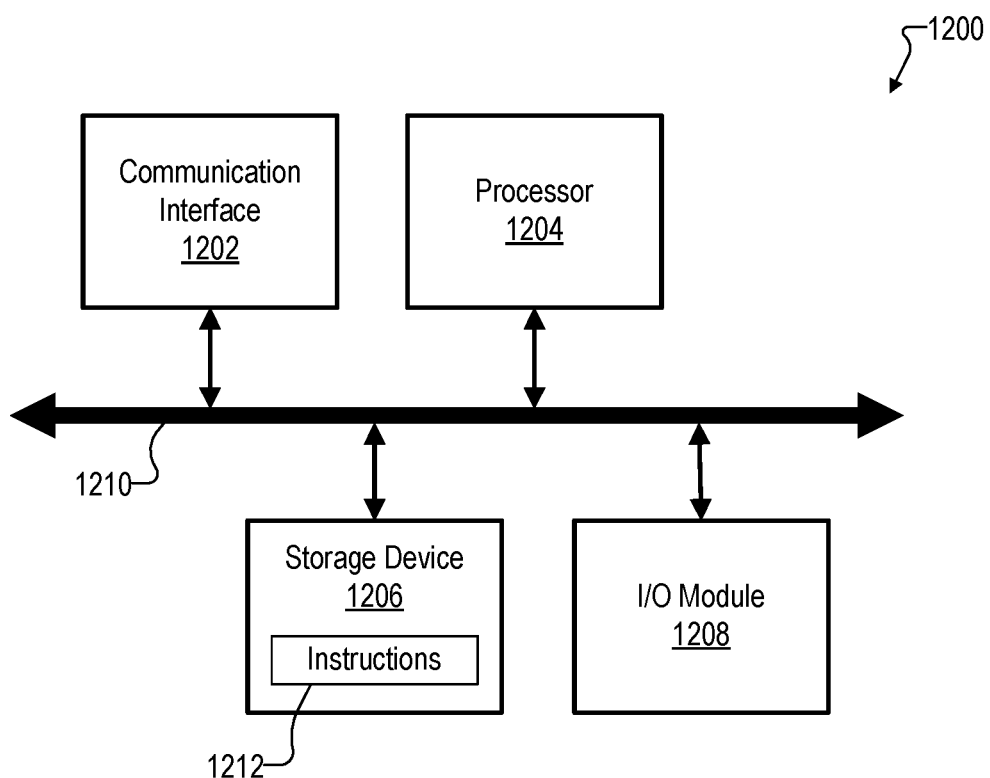
FIG. 12 shows an illustrative computing device according to principles described herein.

FIG. 12 shows an illustrative computing device 1200 that may be specifically configured to perform one or more of the processes described herein. For example, computing device 1200 may include or implement (or partially implement) a research support computing system such as system 100 or any component included therein or system associated therewith (e.g., any of the systems or devices included in configuration 300 of FIG. 3, other systems and devices described herein, etc.).

As shown in FIG. 12, computing device 1200 may include a communication interface 1202, a processor 1204, a storage device 1206, and an input/output (I/O) module 1208 communicatively connected via a communication infrastructure 1210. While an illustrative computing device 1200 is shown in FIG. 12, the components illustrated in FIG. 12 are not intended to be limiting. Additional or alternative components may be used in other embodiments. Components of computing device 1200 shown in FIG. 12 will now be described in additional detail.

Communication interface 1202 may be configured to communicate with one or more computing devices. Examples of communication interface 1202 include, without limitation, a wired network interface (such as a network interface card), a wireless network interface (such as a wireless network interface card), a modem, an audio/video connection, and any other suitable interface.

Processor 1204 generally represents any type or form of processing unit capable of processing data or interpreting, executing, and/or directing execution of one or more of the instructions, processes, and/or operations described herein. Processor 1204 may direct execution of operations in accordance with one or more computer-executable instructions 1212 such as may be stored in storage device 1206 or another computer-readable medium.

Storage device 1206 may include one or more data storage media, devices, or configurations and may employ any type, form, and combination of data storage media and/or device. For example, storage device 1206 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1206. For example, data representative of one or more executable instructions 1212 configured to direct processor 1204 to perform any of the operations described herein may be stored within storage device 1206. In some examples, data may be arranged in one or more databases residing within storage device 1206.

I/O module 1208 may include one or more I/O modules configured to receive user input and provide user output. One or more I/O modules may be used to receive input for a single virtual experience. I/O module 1208 may include any hardware, firmware, software, or combination thereof supportive of input and output capabilities. For example, I/O module 1208 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1208 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1208 is configured to provide graphical data to a display for presentation to a user. The graphical data may be representative of one or more graphical user interfaces and/or any other graphical content as may serve a particular implementation.

In some examples, any of the facilities described herein may be implemented by or within one or more components of computing device 1200. For example, one or more instructions 1212 residing within storage device 1206 may be configured to direct processor 1204 to perform one or more processes or functions associated with processor 104 of system 100. Likewise, memory 102 of system 100 may be implemented by or within storage device 1206.

Figure 13:
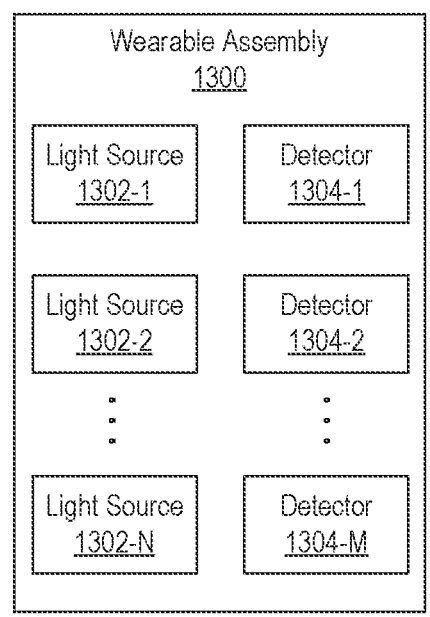
FIG. 13 shows a functional diagram of an exemplary wearable assembly that may implement, or be included in an implementation of, an optical measurement system.

FIG. 13 shows a functional diagram of an exemplary wearable assembly 1300 that may implement, or be included in an implementation of, optical measurement system 1000. Wearable assembly 1300 includes N light sources 1302 (e.g., light sources 1302-1 through 1302-N) and M detectors 1304 (e.g., detectors 1304-1 through 1304-M). Wearable assembly 1300 may include any of the other components of optical measurement system 1000 as may serve a particular implementation. N and M may each be any suitable value (i.e., there may be any number of light sources 1302 and any number of detectors 1304 included in wearable assembly 1300 as may serve a particular implementation).

Light sources 1302 are each configured to emit light (e.g., a sequence of light pulses) and may be implemented by any of the light sources described herein. Detectors 1304 may each be configured to detect arrival times for photons of the light emitted by one or more light sources 1302 after the light is scattered by the target. For example, a detector 1304 may include a photodetector configured to generate a photodetector output pulse in response to detecting a photon of the light and a TDC configured to record a timestamp symbol in response to an occurrence of the photodetector output pulse, the timestamp symbol representative of an arrival time for the photon (i.e., when the photon is detected by the photodetector). Detectors 1304 may be implemented by any of the detectors described herein.

Wearable assembly 1300 may be implemented by any of the wearable devices, wearable module assemblies, and/or wearable units described herein. For example, wearable assembly 1300 may be implemented by a wearable device (e.g., headgear) configured to be worn on a user's head. Wearable assembly 1300 may additionally or alternatively be implemented by a wearable device configured to be worn on any other part of a user's body.

Wearable assembly 1300 may be modular in that one or more components of wearable assembly 1300 may be removed, changed out, or otherwise modified as may serve a particular implementation. Additionally or alternatively, wearable assembly 1300 may be modular such that one or more components of wearable assembly 1300 may be housed in a separate housing (e.g., module) and/or may be movable relative to other components.

Figure 14:
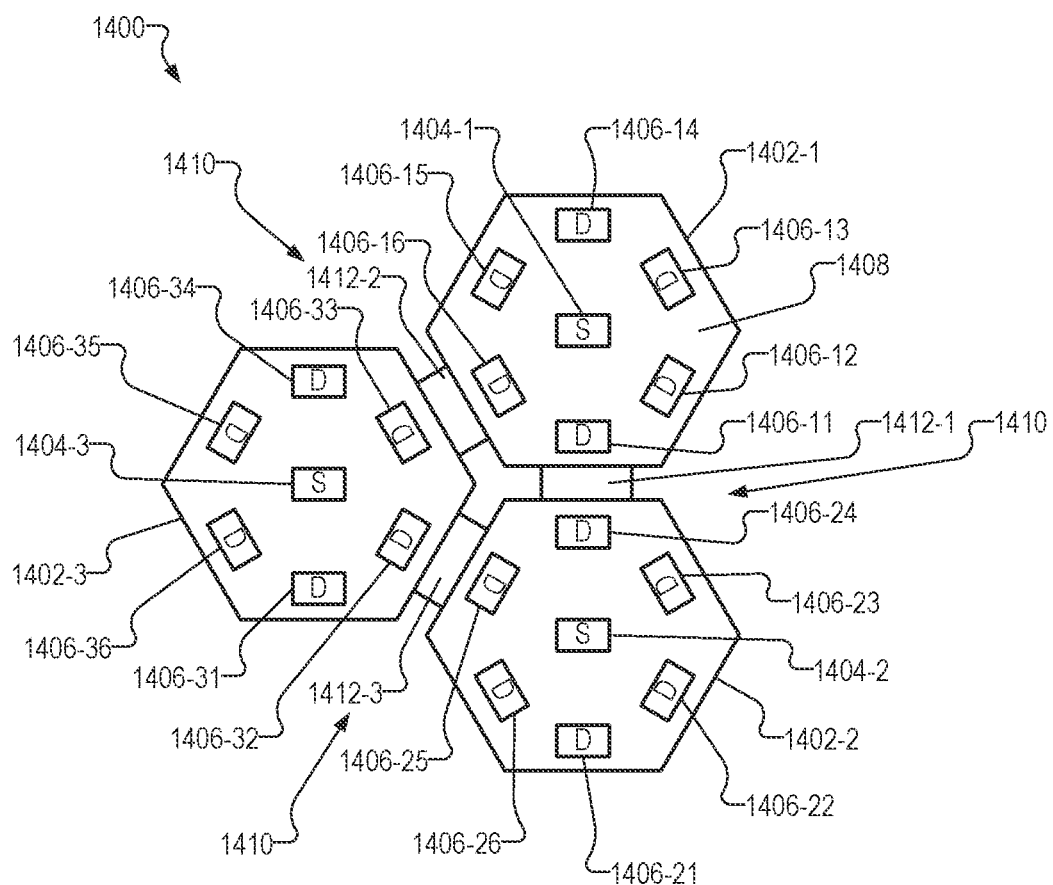
FIG. 14 illustrates an exemplary implementation in which the wearable assembly of FIG. 13 is implemented by a wearable module assembly.

FIG. 14 illustrates an exemplary implementation of wearable assembly 1300. FIG. 14 is illustrative of one of many different implementations of wearable assembly 1300 that may be realized in accordance with the principles described herein. As shown in FIG. 14, wearable assembly 1300 is implemented by a wearable module assembly 1400. Wearable module assembly 1400 includes a plurality of wearable modules 1402 (e.g., modules 1402-1 through 1402-3). Module 1402-1 can represent or include a first module housing, module 1402-2 can represent or include a separate second module housing, module 1403-3 can represent or include a separate third module housing, and so forth. While three modules 1402 are shown to be included in optical measurement system 1300, in alternative configurations, any number of modules 1402 (e.g., a single module up to sixteen or more modules) may be included in wearable module assembly 1400.

Each module 1402 includes a light source 1404 (e.g., light source 1404-1 of module 1402-1, light source 1404-2 of module 1402-2, and light source 1404-3 of module 1402-3) and a plurality of detectors 1406 (e.g., detectors 1406-11 through 1406-16 of module 1402-1, detectors 1406-21 through 1406-26 of module 1402-2, and detectors 1406-31 through 1406-36 of module 1402-3). In the particular implementation shown in FIG. 14, each module 1402 includes a single light source 1404 (labeled "S") and six detectors 1406 (each labeled "D"). However, each module 1402 may have any other number and arrangement of light sources 1404 and detectors 1406 as may serve a particular implementation. Any one or more components of a module 1402 (e.g., a light source 1404, detectors 1406, and/or any other components) may be housed, in whole or in part, within a module housing.

Each light source 1404 may be implemented by any light source described herein and may be configured to emit a light pulse directed at a target (e.g., the brain). For example, light source 1404-1 may emit a first light pulse toward the target and light source 1404-2 may emit a second light pulse toward the target. In some examples, each light source 1404 housed within module 1402 includes one or more light-generating components (e.g., laser diodes). Each light source 1404 may additionally include any suitable optical components (e.g., an optical conduit) configured to guide and direct emitted light toward the target. In some examples, a portion of each light source 1404 (e.g., an optical conduit) protrudes from a front surface 1408 of the module 1402 (e.g., a surface of module 1402 facing, or parallel to a surface of, the body of the user when wearable module assembly 1400 is worn by the user) to facilitate contact of light source 1404 with the body of the user and/or to penetrate through the user's hair.

Each light source 1404 may be located at a center region of front surface 1408. In alternative implementations, a light source 1404 of a module 1402 may be located at any other location on the module. In alternative configurations (not shown) of a module 1402, one or more components of the light source 1404 (e.g., laser diodes) may be located remotely in/on another device separate from module 1402, and the generated light may be conveyed to module 1402 by another optical conduit (e.g., optical fibers, etc.).

Each detector 1406 may be implemented by any detector described herein and may include a plurality of photodetectors (e.g., SPADs) as well as other circuitry (e.g., TDCs, RF antennas, inductive coupling coils) housed within module 1402. Each detector 1406 may be configured to detect arrival times for photons of the light emitted by one or more light sources after the photons are scattered by the target. For example, detector 1406-11 may detect a first set of photons included in the first light pulse after the first set of photons are scattered by the target, and detector 1406-21 may detect a second set of photons included in the second light pulse after the second set of photons are scattered by the target. In some examples, each detector 1406 housed within module 1402 may also include any suitable optical components (e.g., an optical conduit) configured to receive and guide photons scattered by the target toward the plurality of photodetectors included in the detector 1406. In some examples, a portion of each detector 1406 (e.g., an optical conduit) protrudes from front surface 1408 to facilitate contact with the body of the user and/or to penetrate through the user's hair.

In alternative configurations (not shown) of a module 1402, one or more components of a detector 1406 (e.g., a photodetector) may be located remotely in/on another device separate from the module 1402, and the scattered photons received by detector 1406 are conveyed from the module 1402 by another optical conduit (e.g., optical fibers, etc.) to the remote component.

As shown in FIG. 14, the detectors 1406 of a module 1402 may be distributed around light source 1404 of the same module 1402. In this configuration, detectors 1406 may be configured to detect photon arrival times for photons included in light pulses emitted by the light source 1404 and scattered by the target. In some examples, the detectors 1406 of a module 1402 may all be equidistant from the light source 1404 of the same module. That is, the detectors 1406 of a module 1402 are separated from the light source 1404 of the module 1402 by the same source-detector distance. As used herein, the source-detector distance refers to the linear distance between the point where a light pulse emitted by a light source 1404 exits module 1402 (i.e., a distal end (light-emitting) surface of a light-emitting optical conduit of light source 1404) and the point where photons included in the light pulse and scattered by the target enter module 1402 (i.e., a distal end (light-receiving) surface of the light-receiving optical conduit of a detector 1406). Detectors 1406 of a module 1402 may be alternatively disposed on the module 1402 in any other suitable way as may serve a particular implementation.

In some examples, each module 1402 has a rigid construction such that the source-detector distance for all detectors 1406 on the module 1402 is fixed (e.g., the positions of detectors 1406 on the module 1402 are fixed). Additionally, in some examples the source-detector distance for all detectors 1406 among all modules 1402 in wearable module assembly 1400 is the same. Such configuration ensures uniform coverage over the target and simplifies processing of the detected signals as compared with an uneven distribution of sources and detectors. Moreover, maintaining a known, fixed source-detector distance allows subsequent processing of the detected signals to infer spatial (e.g., depth localization, inverse modeling) information about the detected signals. A fixed, uniform source-detector spacing also provides consistent spatial (lateral and depth) resolution across the target area of interest, e.g., brain tissue.

In some configurations, a module 1402 may be formed with a curve along one or more axes. For example, a module 1402 may be slightly curved along two perpendicular axes, thereby improving contact of light source 1404 and detectors 1406 with a curved surface (e.g., the head) of the user's body. Additionally, the curved construction of module 1402 may help prevent loss of contact between light source 1404 and detectors 1406 due to other forces acting on the module 1406, such as pulling by cords, wires, or optical fibers attached to the module 1402, movement of the user, etc.

Wearable module assembly 1400 also includes a connecting assembly 1410 that physically connects individual modules 1402 with one another. In some examples, connecting assembly 1410 flexibly connects modules 1402 such that wearable module assembly 1400 is conformable to a 3D (non-planar) surface, such as a surface of the user's body (e.g., the user's head), when the wearable module assembly 1400 is worn by the user. Connecting assembly 1410 may be implemented by any suitable device, structure, connectors, or mechanism as may suit a particular implementation.

For example, as shown in FIG. 14, connecting assembly 1410 is implemented by a plurality of connectors 1412 (e.g., connectors 1412-1 to 1412-3) between adjacent modules 1402. Connectors 1412 may be implemented by any suitable connecting mechanisms that flexibly connect adjacent modules 1402, such as hinges, flexible straps (e.g., elastic bands, fabric straps, cords, etc.), ball joints, universal joints, snap-fit connections, and the like.

In some examples, connectors 1412 may be attached to modules 1402 at mutually-facing side surfaces of modules 1402. Additionally or alternatively, connectors 1412 may be attached to each module 1402 at front surfaces 1408 and/or on back surfaces of modules 1402 (e.g., surfaces facing away from the body of the user when wearable module assembly 1400 is worn by the user). Connectors 1412 may be attached to modules 1402 in any suitable way, such as by fasteners (e.g., screws), adhesion, magnets, hook-and-loop, snap-fit connections, and any other suitable attachment mechanism. In some examples, a module 1402 may be removably attached to connectors 1412 such that the module 1402 may be easily attached to and/or removed from wearable assembly 1402. In some examples, connectors 1412 are integrally formed with modules 1402 (e.g., with housings of modules 1402).

Connectors 1412 may permit movement of a module 1402 relative to an adjacent, connected module 1402 in one or more degrees of freedom. For instance, a hinge connector may enable movement (rotation) of a module 1402 about a single axis that is parallel to adjacent, facing edges of modules 1402. A flexible strap may provide up to three degrees of translational movement and/or up to three degrees of rotational movement of a module 1402 relative to an adjacent, connected module 1402.

In some examples, connecting assembly 1410 (e.g., connectors 1412) prohibits translational movement of modules 1402 toward/away from one another to thereby maintain a substantially uniform spacing of all adjacent modules 1402 as well as a uniform spacing of light sources 1404 and detectors 1406. In such configurations, the spacing between a light source 1404 on a first module and detectors 1406 that are positioned at similar positions on all adjacent modules may be maintained at a fixed, uniform distance. For example, the source-detector distance between light source 1404-1 and detectors 1406-24 and 1406-33 is the same fixed distance, and the source-detector distance between light source 1404-1 and detectors 1406-23, 1406-25, 1406-32, 1406-34 is the same fixed distance.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
maintaining, by a research support computing system, subject data representative of respective sets of attributes for a plurality of research subjects included in a potential subject pool for potential research studies;
receiving, by the research support computing system from a client device, an input dataset that the client device receives from a brain researcher using the client device, the input dataset representative of:
a set of parameters defining a brain research study to be conducted with respect to a research subject group, and
a set of criteria for research subjects that are to be included in the research subject group;
designating, by the research support computing system based on the set of criteria and the subject data, a research subject included in the potential subject pool for inclusion in the research subject group;
receiving, by the research support computing system from a brain interface system used by the research subject designated for inclusion in the research subject group, research data detected for the research subject in accordance with the set of parameters, wherein:
the brain interface system is a non-invasive, optical-based brain interface system comprising a wearable module assembly that includes a plurality of modules configured to detect the research data when the wearable module assembly is worn on a head of the research subject,
each module of the plurality of modules is housed in a separate respective housing and is removably attached to the wearable module assembly so as to be capable of being changed out with other modules and moved relative to other modules, and
each module of the plurality of modules includes a light source and a plurality of photodetectors each configured to detect photons generated by the light source after the photons are scattered by a target within a brain of the research subject; and
providing, by the research support computing system, an output dataset generated based on the research data detected for the research subject in accordance with the set of parameters.

2. The method of claim 1, further comprising providing, by the research support computing system, a computer interface that includes a graphical user interface including:
a first graphical element configured for use by the brain researcher to input a parameter of the set of parameters defining the brain research study;
a second graphical element configured for use by the brain researcher to input a first criterium associated with a demographic attribute for the research subjects that are to be included in the research subject group; and
a third graphical element configured for use by the brain researcher to input a second criterium associated with an experience-related attribute indicating a particular industry of current or past employment for the research subjects that are to be included in the research subject group.

3. The method of claim 2, wherein:
the parameter that is input using the first graphical element defines an aspect of an experimental design of the brain research study;
the first criterium associated with the demographic attribute and that is input using the second graphical element defines at least one of a gender, an age range, an ethnicity, a nationality, or a geography of residence that is to characterize each research subject designated for inclusion in the research subject group; and
the graphical user interface further includes a fourth graphical element configured for use by the brain researcher to input an additional criterium of the set of criteria, the additional criterium defining an additional attribute that is not to characterize any research subject designated for inclusion in the research subject group.

4. The method of claim 2, wherein the graphical user interface further includes a fourth graphical element configured to output, for display to the brain researcher, status data indicative of a current status of the brain research study.

5. The method of claim 1, further comprising providing, by the research support computing system, a computer interface that includes at least one of an application programming interface (API) or a software development kit (SDK).

6. The method of claim 1, wherein the designating of the research subject for inclusion in the research subject group includes:
   determining that the research subject satisfies the set of criteria;
   transmitting, based on the determining that the research subject satisfies the set of criteria, data representative of a study participation offer to a subject device used by the research subject;
   receiving, subsequent to the transmitting of the data representative of the study participation offer, data representative of a study participation acceptance from the subject device; and
   selecting, in response to the receiving of the data representative of the study participation offer, the research subject for inclusion in the research subject group.

7. The method of claim 1, wherein the designating of the research subject for inclusion in the research subject group includes:
   determining that the research subject satisfies the set of criteria;
   selecting, based on the determining that the research subject satisfies the set of criteria, the research subject for inclusion in the research subject group; and
   transmitting, based on the selecting of the research subject, data representative of a study participation assignment to a subject device used by the research subject.

8. The method of claim 1, further comprising automatically facilitating, by the research support computing system based on the set of parameters received in the input dataset, a regulatory approval process associated with the brain research study.

9. The method of claim 8, wherein the automatic facilitating of the regulatory approval process includes:
   determining that preapproval for research studies characterized by the set of parameters defining the brain research study has already been obtained; and
   providing, to the client device based on the determining that the preapproval has already been obtained, an indication of regulatory approval for the brain research study.

10. The method of claim 8, wherein the automatic facilitating of the regulatory approval process includes:
    determining that preapproval for research studies characterized by the set of parameters defining the brain research study has not yet been obtained;
    preparing, based on the set of parameters defining the brain research study and based on the determining that the preapproval has not yet been obtained, an application configured to be submitted as part of the regulatory approval process; and
    providing, to the client device, data representative of the prepared application configured to be submitted as part of the regulatory approval process.

11. The method of claim 8, wherein the automatic facilitating of the regulatory approval process includes:
    determining that preapproval for research studies characterized by the set of parameters defining the brain research study has not yet been obtained;
    preparing, based on the set of parameters defining the brain research study and based on the determining that the preapproval has not yet been obtained, an application configured to be submitted as part of the regulatory approval process; and
    submitting, to a computing system associated with a regulatory approval authority, data representative of the prepared application.

12. The method of claim 1, wherein the output dataset is provided to the client device and includes the research data detected for the research subject in an unprocessed form configured to allow for the research data to be processed by at least one of:
    the client device; or
    a computing system that receives the research data from the client device.

13. The method of claim 1, further comprising processing, by the research support computing system subsequent to the receiving of the research data, the research data detected for the research subject to produce results data that is derived from and different than the research data;
    wherein the output dataset is provided to the client device and includes the results data that is derived from and different than the research data.

14. The method of claim 13, wherein the processing of the research data includes a source reconstruction analysis that estimates, based on the research data detected for the research subject, one or more sources, within a brain of the research subject, that generated one or more signals represented by the research data detected for the research subject.

15. The method of claim 13, wherein the processing of the research data includes a connectivity analysis that defines a spatiotemporal activation pattern across a plurality of regions of a brain of the research subject to indicate a relationship between neural oscillations and functional connectivity of the brain.

16. The method of claim 1, wherein the brain interface system is used by the research subject at a site remote from the research support computing system.

17. The method of claim 1, wherein the brain interface system is used by the research subject at a site of the research support computing system.

18. A system comprising:
    a memory storing instructions; and
    a processor communicatively coupled to the memory and configured to execute the instructions to:
      maintain subject data representative of respective sets of attributes for a plurality of research subjects included in a potential subject pool for potential research studies;
      receive, from a client device, an input dataset that the client device receives from a brain researcher using the client device, the input dataset representative of:
        a set of parameters defining a brain research study to be conducted with respect to a research subject group, and
        a set of criteria for research subjects that are to be included in the research subject group;
      designate, based on the set of criteria and the subject data, a research subject included in the potential subject pool for inclusion in the research subject group;

receive, from a brain interface system used by the research subject designated for inclusion in the research subject group, research data detected for the research subject in accordance with the set of parameters, wherein:
  the brain interface system is a non-invasive, optical-based brain interface system comprising a wearable module assembly that includes a plurality of modules configured to detect the research data when the wearable module assembly is worn on a head of the research subject,
  each module of the plurality of modules is housed in a separate respective housing and is removably attached to the wearable module assembly so as to be capable of being changed out with other modules and moved relative to other modules, and
  each module of the plurality of modules includes a light source and a plurality of photodetectors each configured to detect photons generated by the light source after the photons are scattered by a target within a brain of the research subject; and
provide an output dataset generated based on the research data detected for the research subject in accordance with the set of parameters.

19. The system of claim 18, wherein the processor is further configured to execute the instructions to provide a computer interface that includes a graphical user interface including:
  a first graphical element configured for use by the brain researcher to input a parameter of the set of parameters defining the brain research study;
  a second graphical element configured for use by the brain researcher to input a first criterium associated with a demographic attribute for the research subjects that are to be included in the research subject group; and
  a third graphical element configured for use by the brain researcher to input a second criterium associated with an experience-related attribute indicating a particular industry of current or past employment for the research subjects that are to be included in the research subject group.

20. The system of claim 19, wherein:
  the parameter that is input using the first graphical element defines an aspect of an experimental design of the brain research study;
  the first criterium associated with the demographic attribute and that is input using the second graphical element defines at least one of a gender, an age range, an ethnicity, a nationality, or a geography of residence that is to characterize each research subject designated for inclusion in the research subject group; and
  the graphical user interface further includes a fourth graphical element configured for use by the brain researcher of the client device to input an additional criterium of the set of criteria, the additional criterium defining an additional attribute that is not to characterize any research subject designated for inclusion in the research subject group.

21. The system of claim 19, wherein the graphical user interface further includes a fourth graphical element configured to output, for display to the brain researcher, status data indicative of a current status of the brain research study.

22. The system of claim 18, wherein the processor is further configured to execute the instructions to provide a computer interface that includes at least one of an application programming interface (API) or a software development kit (SDK).

23. The system of claim 18, wherein the designating of the research subject for inclusion in the research subject group includes:
  determining that the research subject satisfies the set of criteria;
  transmitting, based on the determining that the research subject satisfies the set of criteria, data representative of a study participation offer to a subject device used by the research subject;
  receiving, subsequent to the transmitting of the data representative of the study participation offer, data representative of a study participation acceptance from the subject device; and
  selecting, in response to the receiving of the data representative of the study participation offer, the research subject for inclusion in the research subject group.

24. The system of claim 18, wherein the designating of the research subject for inclusion in the research subject group includes:
  determining that the research subject satisfies the set of criteria;
  selecting, based on the determining that the research subject satisfies the set of criteria, the research subject for inclusion in the research subject group; and
  transmitting, based on the selecting of the research subject, data representative of a study participation assignment to a subject device used by the research subject.

25. The system of claim 18, wherein the processor is further configured to execute the instructions to automatically facilitate, based on the set of parameters received in the input dataset, a regulatory approval process associated with the brain research study.

26. The system of claim 25, wherein the automatic facilitating of the regulatory approval process includes:
  determining that preapproval for research studies characterized by the set of parameters defining the brain research study has already been obtained; and
  providing, to the client device based on the determining that the preapproval has already been obtained, an indication of regulatory approval for the brain research study.

27. The system of claim 25, wherein the automatic facilitating of the regulatory approval process includes:
  determining that preapproval for research studies characterized by the set of parameters defining the brain research study has not yet been obtained;
  preparing, based on the set of parameters defining the brain research study and based on the determining that the preapproval has not yet been obtained, an application configured to be submitted as part of the regulatory approval process; and
  providing, to the client device, data representative of the prepared application configured to be submitted as part of the regulatory approval process.

28. The system of claim 25, wherein the automatic facilitating of the regulatory approval process includes:
  determining that preapproval for research studies characterized by the set of parameters defining the brain research study has not yet been obtained;
  preparing, based on the set of parameters defining the brain research study and based on the determining that the preapproval has not yet been obtained, an application configured to be submitted as part of the regulatory approval process; and
  submitting, to a computing system associated with a regulatory approval authority, data representative of the prepared application.

29. The system of claim 18, wherein the output dataset is provided to the client device and includes the research data detected for the research subject in an unprocessed form configured to allow for the research data to be processed by at least one of:

the client device; or a computing system that receives the research data from the client device.

30. The system of claim 18, wherein the processor is further configured to execute the instructions to process, subsequent to the receiving of the research data, the research data detected for the research subject to produce results data that is derived from and different than the research data;

wherein the output dataset is provided to the client device and includes the results data that is derived from and different than the research data.

\* \* \* \* \*